US011696696B2

(12) United States Patent
Kline et al.

(10) Patent No.: US 11,696,696 B2
(45) Date of Patent: Jul. 11, 2023

(54) DISPOSABLE SENSING ELEMENTS COMPRISING A PIEZOELECTRIC UNIT

(71) Applicant: CVR Global, Inc., Denver, NC (US)

(72) Inventors: Bret Kline, Columbus, OH (US); Peter Bakema, Denver, NC (US); Young Truong, Carrboro, NC (US); Richard Finlayson, Greenville, NC (US); Orville Day, Greenville, NC (US)

(73) Assignee: CVR Global, Inc., Denver, NC (US)

( * ) Notice: Subject to any disclaimer, the term of this patent is extended or adjusted under 35 U.S.C. 154(b) by 1245 days.

(21) Appl. No.: 16/309,773

(22) PCT Filed: Jun. 15, 2017

(86) PCT No.: PCT/US2017/037726
§ 371 (c)(1),
(2) Date: Dec. 13, 2018

(87) PCT Pub. No.: WO2017/218807
PCT Pub. Date: Dec. 21, 2017

(65) Prior Publication Data
US 2019/0254539 A1 Aug. 22, 2019

Related U.S. Application Data

(60) Provisional application No. 62/350,617, filed on Jun. 15, 2016.

(51) Int. Cl.
*A61B 7/00* (2006.01)
*A61B 5/026* (2006.01)
*A61B 5/0285* (2006.01)
*A61B 5/02* (2006.01)
*A61B 5/00* (2006.01)
*A61B 7/04* (2006.01)
*A61B 5/11* (2006.01)
*A61B 5/333* (2021.01)

(52) U.S. Cl.
CPC ............ *A61B 5/0285* (2013.01); *A61B 5/026* (2013.01); *A61B 5/02007* (2013.01); *A61B 5/1102* (2013.01); *A61B 5/333* (2021.01); *A61B 5/6811* (2013.01); *A61B 5/6822* (2013.01); *A61B 5/6823* (2013.01); *A61B 7/00* (2013.01); *A61B 7/045* (2013.01); *A61B 2562/0204* (2013.01)

(58) Field of Classification Search
None
See application file for complete search history.

(56) References Cited

U.S. PATENT DOCUMENTS 5,960,089 A * 9/1999 Bouricius ................ A61B 7/04
381/67
9,101,274 B2 8/2015 Bakema et al.
2002/0072684 A1 6/2002 Stearns
(Continued)

FOREIGN PATENT DOCUMENTS

WO WO/2016/205365 12/2016

*Primary Examiner* — Meredith Weare
(74) *Attorney, Agent, or Firm* — Vos-IP, LLC

(57) ABSTRACT

A device for detecting stenosis comprising disposable components to ensure function and sanitary conditions, said device having a disposable sensing pad, a disposable piezo assembly, and a disposable sensing pod; wherein the entire device can be disposed of after a predetermined number of uses to ensure accuracy of results and of sanitary conditions.

9 Claims, 19 Drawing Sheets

(56) References Cited

U.S. PATENT DOCUMENTS

| | | | |
|---|---|---|---|
| 2003/0196660 A1* | 10/2003 | Haveri | A61M 16/147 128/203.12 |
| 2011/0137210 A1 | 6/2011 | Johnson | |
| 2012/0232427 A1* | 9/2012 | Bakema | A61B 7/003 600/586 |
| 2014/0081175 A1 | 3/2014 | Telfort | |

* cited by examiner

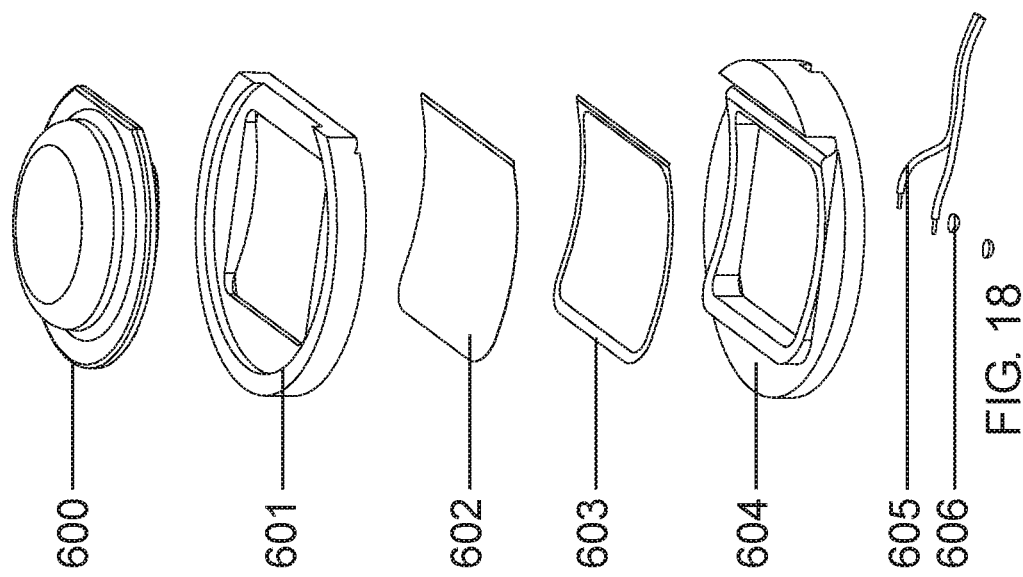
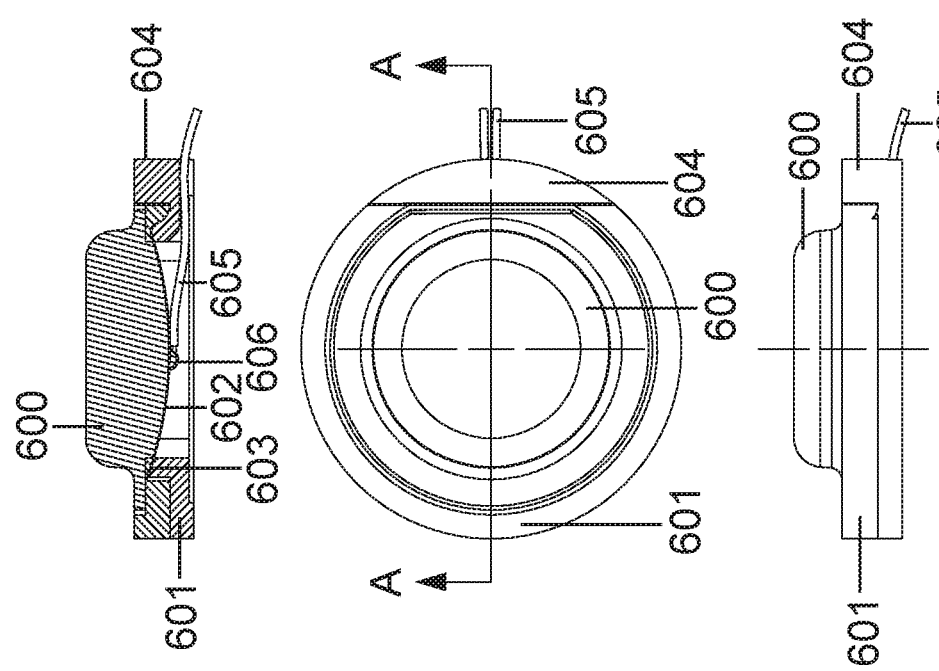

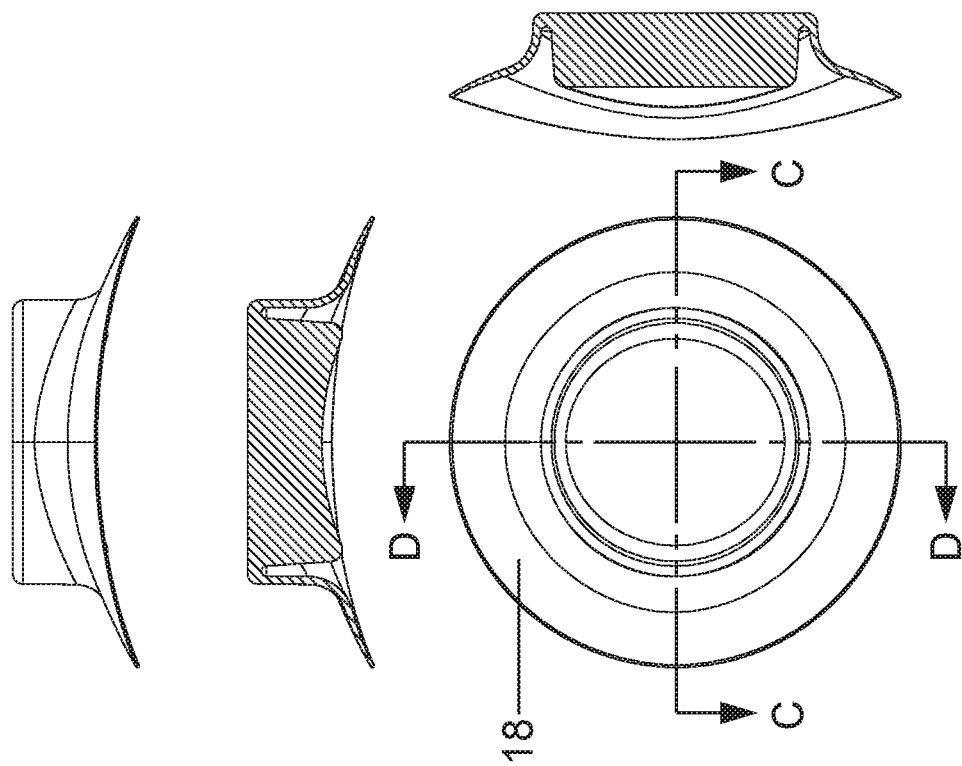
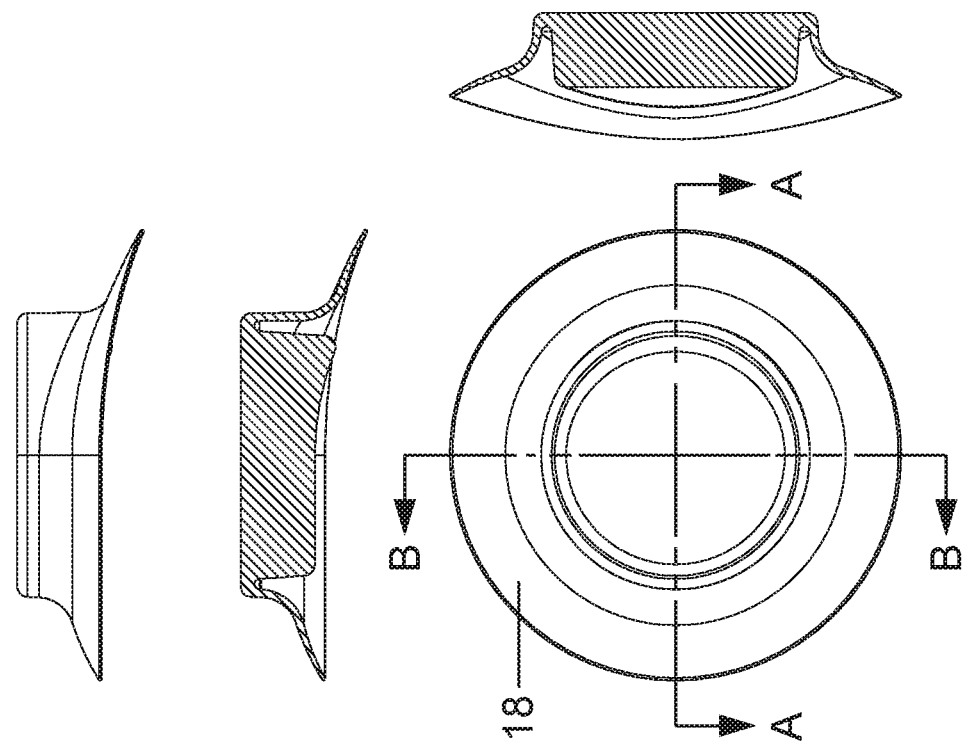
FIG. 19

DISPOSABLE SENSING ELEMENTS COMPRISING A PIEZOELECTRIC UNIT

CROSS-REFERENCE TO RELATED APPLICATION

This application is a 371 of PCT Application No. PCT/US2017/037726, filed Jun. 15, 2017, which claims the benefit of U.S. Provisional Application Ser. No. 62/350,617, filed Jun. 15, 2016, the disclosure content of which is hereby incorporated by reference in its entirety.

FIELD OF INVENTION

The present application is generally related to disposable components for detecting blockage in a fluid flow vessel. In particular, the application is directed towards a disposable sensor pod that configures to a sensing device, wherein said disposable sensor comprises a piezoelectric component that is utilized on a sensing device to be positioned on the skin of a patient for detecting acoustic sound from the flow of bodily fluids. Additional disposable components include a disposable sensor pod and a disposable array.

BACKGROUND

Piezoelectric units function based on the occurrence of electric dipole moments in solids. The solid may be either induced for ions on crystal lattice sites with asymmetric charge surroundings, or may directly be carried by molecular groups. The dipole density or polarization may be calculated by summing up the dipole moment per volume of the crystallographic unit cell.

There is a need to sterilize equipment in all medical settings. Medical devices should be sterile to prevent transmission of bacteria and disease. As such, medical devices are typically cleaned or, where not possible, replaced entirely. Cleaning solvents are frequently harsh chemicals to ensure high kill rates of bacterial and viral loads that may be transmitted by touch. Accordingly, devices that are re-used need to be able to support the rigors of these chemicals.

Like all components, piezo elements wear over time from ordinary use. Furthermore, accidental damage can and will occur, and thus replacement components are necessary to ensure that devices are not out of order for longer than necessary. Furthermore, because of the sensitive nature of the piezo, it is necessary to ensure that they are properly functioning before each use. Accordingly, the piezos must be designed to allow for easy replacement of the piezo, while ensuring that a device maintains operation and reliability during ordinary use.

SUMMARY OF THE INVENTION

The summary is provided as non-limiting examples of the embodiments of the invention. Each of the embodiments can be combined with the other additional embodiments without deviating from the scope of the invention as envisioned by the inventors. Additionally components of one embodiment can be combined with components of another embodiment as described herein and as understood by a person of ordinary skill in the art. Accordingly, a first embodiment is directed to a disposable sensor, comprising a piezoelectric element ("Piezo"), a cap, and a contact board. The sensor is mounted to the cap on one card, and the contact board mounted on the opposing end of the cap, wherein the cap comprises attachment means to secure to a base component, together defining a sensor pod.

A further embodiment is directed towards a disposable sensor assembly comprising a piezoelectric sensor, a contact board, and a circular shaped housing cap, having a top side and a bottom side, an inner surface and an outer surface, and a central opening extending through the top and bottom sides, on the top side a flange is positioned inside the central opening and disposed of to receive said piezoelectric sensor around the circumference of said piezoelectric sensor; the bottom side engaging said contact board which is secured beneath the flange; and one-half of a locking means on said inner surface. In preferred embodiments, the one-half of a locking means connects to a paired locking means, forcing contact with the contact board and powering the piezo. However, upon need for replacement, said disposable sensor assembly is quickly and easily withdrawn and replaced.

A further embodiment is directed towards a disposable sensor pod, comprising a piezo, a cap, a contact board, a PCB processor board, and a PCB housing, wherein the PCB housing comprises attachments to secure to an array, suitable for placing said sensor pod on a patient.

A further embodiment is directed towards a disposable sensor pod comprising a disposable sensor assembly and a disposable sensor base assembly, said disposable sensor base assembly comprising a PCB processor board, a PCB housing, a diaphragm bellows membrane, locking means to secure said diaphragm bellows membrane, and a locking cap, wherein attachment means are provided to allow said disposable sensor base assembly to engage to and disengage from an array device.

A further embodiment is directed towards a disposable sensor pod comprising a piezo, a cap, a contact board, a PCB processor board, a PCB housing, a diaphragm bellows membrane (DBM) and a locking cap, wherein said piezo, cap and contact board are secured to the PCB housing, which forces contact between the contact board and the PCB processor board, and on an opposing end of the PCB housing, the DBM is defined through an aperture y device, and secured to said array with a locking cap that secures said DBM to said array device, with the DBM being positioned through said aperture allowing movement of the disposable sensor pod.

A further embodiment is directed towards a disposable sensor pod comprising a diaphragm bellow membrane (DBM), said DBM comprising a top, a bottom, and outer edge comprising a flange, and an opening, between said top and bottom, with an inner flange around said opening; said DMB being secured at the outer flange between an inner and outer array; and said inner flange being secured between a locking cap and a PCB housing; wherein a disposable sensor assembly engages to and selectively engages the PCB housing. In certain embodiments, the disposable sensor assembly comprises a piezoelectric sensor, a contact board, and a circular shaped housing cap, having a top side and a bottom side, an inner surface and an outer surface, and a central opening extending through the top and bottom sides, on the top side a flange is positioned inside the central opening and disposed of to receive said piezoelectric sensor around the circumference of said piezoelectric sensor; the bottom side engaging said contact board which is secured beneath the flange; and one-half of a locking means on said inner surface. In preferred embodiments, the one-half of a locking means connects to a paired locking means, forcing contact with the contact hoard and powering the piezo. However, upon need for replacement, said disposable sensor assembly is quickly and easily withdrawn and replaced.

A further embodiment is directed towards a disposable sensor array comprising a track structure for securing at least two sensor pods; a disposable sensor pod comprising a sensor base having an track engaging means for selectively engaging to a slideably attaching to said track structure; said disposable sensor pod comprising a disposable piezo sensor and a PCB board. In certain embodiments said disposable sensor pod comprises a diaphragm bellow membrane (DBM), said DBM comprising a top a bottom and outer edge comprising a flange, and an opening, between said top and bottom, with an inner flange around said opening; said DMB being secured at the outer flange between an inner and outer array; and said inner flange being secured between a locking cap and a PCB housing; wherein a disposable sensor assembly engages to and selectively engages the PCB housing. In certain embodiments, the disposable sensor assembly comprises a piezoelectric sensor, a contact board, and a circular shaped housing cap, having a top side and a bottom side, an inner surface and an outer surface, and a central opening extending through the top and bottom sides, on the top side a flange is positioned inside the central opening and disposed of to receive said piezoelectric sensor around the circumference of said piezoelectric sensor; the bottom side engaging said contact board which is secured beneath the flange; and one-half of a locking means on said inner surface. In preferred embodiments, the one-half of a locking means connects a paired locking means, forcing contact with the contact board and powering the piezo. However, upon need for replacement, said disposable sensor assembly is quickly and easily withdrawn and replaced.

A further embodiment is directed towards a disposable sensor array comprising a track structure for securing at least two sensor pods; a disposable sensor pod comprising a sensor base having a track engaging means for selectively engaging to a slideably attaching to said track structure. A further embodiment is directed to disposable curved sensor pads that are configured to selectively secure to a sensor pod, and which are replaceable units for use with an individual patient. The sensor pads are made from a silicon like gel material and are molded into a predetermined shape, wherein the predetermined shape aids in transmitting sound waves from the body to the piezo elements and also in blocking out extraneous noise to prevent debris and noise within the signal and data to be analyzed.

A further embodiment is directed towards a disposable array for determining carotid artery stenosis in a human patient comprising: a stem; a neck coupled to the stem and defining an angle of between 125° and 175°; a neck vertex coupled to the neck opposite the stem; and a pair of arms extending from the neck vertex, the pair of arms defining an angle of between 90° and 145°, and wherein each of the legs and arms are made of a flexible material that is configured to be flexed away from its resting state; and wherein the flexible plastic material imparts a force to return back to its resting state. A further embodiment is directed towards the array wherein the stem and arms define a track section. A further embodiment is directed towards the array wherein each of the arms and the stem are configured to receive a sensor pod.

A further embodiment is directed towards the array for determining carotid artery steno sis in the human patient wherein each of the sensor pods comprises: a housing configured to be coupled to the arms and the stem; a disposable cap configured to removeably attach to the housing; a diaphragm that extends out of the disposable cap; a printed circuit board having integrated circuits, a rechargeable battery, spring loaded contact, an input, and LED status lights arranged thereon; a piezo element configured to receive vibrations from the diaphragm and output a signal to the input of the printed circuit board; and, optionally, a wireless charging coil configured to inductively charge the rechargeable battery.

A further embodiment is directed towards a disposable array for use in a carotid artery sensor configured as a Y-shaped structure comprising: a neck; a stem; a stem vertex arranged between the neck and the stem; a neck vertex coupled to the neck opposite the stem vertex; a left and a right arm coupled to the neck vertex, wherein the neck and stem are connected via the stem vertex such that the neck is biased at an angle of about 165 degrees; wherein the left and right arms extend substantially perpendicularly from the neck from the neck vertex, and wherein the left and right arms create a bell-like shape. A further embodiment is directed towards the array wherein each of the arms and the stem define a track like structure are configured to receive a sensor pod. A further embodiment is directed towards the array wherein the sensor pod comprises: a housing configured to be coupled to the arms and the stem; a friction plunger defined to secure the sensor pod to the track like structure on the array; a disposable cap configured to removeably attach to the housing; a diaphragm that extends out of the disposable cap; a printed circuit board having integrated circuits, a rechargeable battery, spring loaded contact, an input, and LED status lights arranged thereon; a piezo element configured to receive vibrations from the diaphragm and output a signal to the input of the printed circuit board; and, optionally, a wireless charging coil configured to inductively charge the rechargeable battery.

A further embodiment is directed towards a disposable piezo assembly comprising: a circular piezo cap comprising a top and a bottom an inner face and an outer face, with an opening between the top and bottom with the opening larger at the top than the opening at the bottom; a flange positioned on the inner face of the opening; a piezo having a top, a bottom, and a perimeter support; said piezo disposed of within said opening, with the bottom of the perimeter support engaged to an adhered to said flange; a printed circuit board having a ring shape and an outer diameter to fit within the opening and engaged to the bottom of said flange; and on said inner face one-half of an attachment means for securing said disposably piezo assembly to an assembly base.

A further embodiment is directed towards a sensor base for connecting to an array comprising a diaphragm bellows membrane a printed circuit board housing, a printed circuit board, and a cap; said diaphragm bellows membrane being a ring shape having an outer flange on an outer circumference of said ring, and an inner flange on an inner circumference of said ring; said outer flange engaging to said array and said inner flange engaging between said cap and said printed circuit board housing; said printed circuit board housing comprising a bell shape, having a narrow bottom and a wide top, with an opening between the top and bottom, a locking groove on said narrow bottom to engage said inner flange; and an attachment means a the top of the top; said printed circuit board fitting within said opening. In certain embodiments, the attachment means being a magnet, one-half of a quarter turn locking mechanism; a groove, a pin, or threading.

A further embodiment is directed towards a disposable sensor pod comprising disposable piezo assembly and a sensor base, said disposable piezo assembly comprising: a circular piezo cap comprising a top and a bottom, an inner face and an outer face, with an opening between the top and bottom with the opening larger at the top than the opening at the bottom; a flange positioned on the inner face of the opening; a piezo having a top, a bottom, and a perimeter support; said piezo disposed of within said opening, with the bottom of the perimeter support engaged to an adhered to said flange; a printed circuit board having a ring shape and an outer diameter to fit within the opening and engaged to the bottom of said flange; and on said inner face one-half of an attachment means for securing said disposably piezo assembly to said sensor base; and said sensor base comprising a diaphragm bellows membrane, a printed circuit board housing, a printed circuit board, and a cap; said diaphragm bellows membrane being a ring shape having an outer flange on an outer circumference of said ring, and an inner flange on an inner circumference of said ring; said outer flange engaging to said array and said inner flange engaging between said cap and said printed circuit board housing; said printed circuit board housing comprising a bell shape, having a narrow bottom and a wide top, with an opening between the top and bottom, a locking groove on said narrow bottom to engage said inner flange; and an attachment means at the top of the top; said printed circuit board fitting within said opening.

A further embodiment is directed towards a disposable array comprising an array body, and three sensor pods; said array body comprising an inner array half and an outer array half, each inner and outer half comprising two arms and a neck; and three openings defined at each end of the arms and neck; said openings defined to accept a diaphragm bellows membrane, wherein said diaphragm bellows membrane comprises an outer flange to be accepted between said inner array half and outer array half; and a disposable sensor pod comprising a disposable piezo assembly and a sensor base, said disposable piezo assembly comprising: a circular piezo cap comprising a top and a bottom, an inner face and an outer face, with an opening between the top and bottom with the opening larger at the top than the opening at the bottom; a flange positioned on the inner face of the opening; a piezo having a top, a bottom, and a perimeter support; said piezo disposed of within said opening, with the bottom of the perimeter support engaged to an adhered to said flange; a printed circuit board having a ring shape and an outer diameter to fit within the opening and engaged to the bottom of said flange; and on said inner face one-half of an attachment means for securing said disposably piezo assembly to said sensor base; and said sensor base comprising a diaphragm bellows membrane, a printed circuit board housing, a printed circuit board, and a cap; said diaphragm bellows membrane being a ring shape having an outer flange on an outer circumference of said ring, and an inner flange on an inner circumference of said ring; said outer flange engaging between said inner array half and said outer array half in each of said three openings, and said inner flange engaging between said cap and said printed circuit board housing; said printed circuit board housing comprising a bell shape, having a narrow bottom and a wide top, with an opening between the top and bottom, a locking groove on said narrow bottom to engage said inner flange; and an attachment means at the top of the top; said printed circuit board fitting within said opening.

A further embodiment is directed towards a disposable array comprising a track body for accepting at least two sensor pods; said disposable array defined in a "C" like shape, wherein the track body receives a sensor having a track accepting opening, and wherein said sensor is capable of being positioned on said array by sliding said sensor along said track.

A further embodiment is directed towards a slideable disposable sensor pod comprising a disposable piezo assembly and a track accepting base end, comprising an opening defined to position on a track structure of an array; said disposable piezo assembly comprising: a circular piezo cap comprising a top and a bottom, an inner face and an outer face, with an opening between the top and bottom with the opening larger at the top than the opening at the bottom; a flange positioned on the inner face of the opening; a piezo having a top, a bottom, and a perimeter support; said piezo disposed of within said opening, with the bottom of the perimeter support engaged to an adhered to said flange; a printed circuit board having a ring shape and an outer diameter to fit within the opening and engaged to the bottom of said flange; and on said inner face one-half of an attachment means for securing said disposably piezo assembly to said sensor base; and said sensor base comprising a diaphragm bellows membrane, a printed circuit board housing, a printed circuit board, and a cap; said diaphragm bellows membrane being a ring shape having an outer flange on an outer circumference of said ring, and an inner flange on an inner circumference of said ring; said outer flange engaging to a locking groove in said track accepting base end; and said inner flange engaging between said cap and said printed circuit board housing; said printed circuit board housing comprising a bell shape, having a narrow bottom and a wide top, with an opening between the top and bottom, a locking groove on said narrow bottom to engage said inner flange; and an attachment means at the top of the top; said printed circuit board fitting within said opening.

A further embodiment is directed towards a slideable sensor pod comprising a piezo cap defining an opening between a top and bottom, a flange in said top, disposed to accept a piezo through said bottom and secure adjacent to said flange; a printed circuit contact board engaging electrical contacts between said piezo and a printed circuit board positioned below said piezo; a knuckle having an opening between a top and bottom, with said top opening receiving said printed circuit board and the bottom opening receiving a sled ball; said sled ball comprising a top having a globular shape to match the shape of the opening in the bottom of said knuckle, and a bottom defined to slide along a track of an array; a compression spring and compression washer engaging the knuckle and said sled ball to allow for movement of the sled ball to orient the sensor pod at angles from the sled ball.

BRIEF DESCRIPTION OF THE DRAWINGS

FIG. 17 depicts a sensor paid with a curved, concave piezo.

FIG. 18 depicts a concave piezo.

FIG. 19 depicts non-symmetrical sensor pads.

DETAILED DESCRIPTION OF THE PREFERRED EMBODIMENTS

Figure 1:
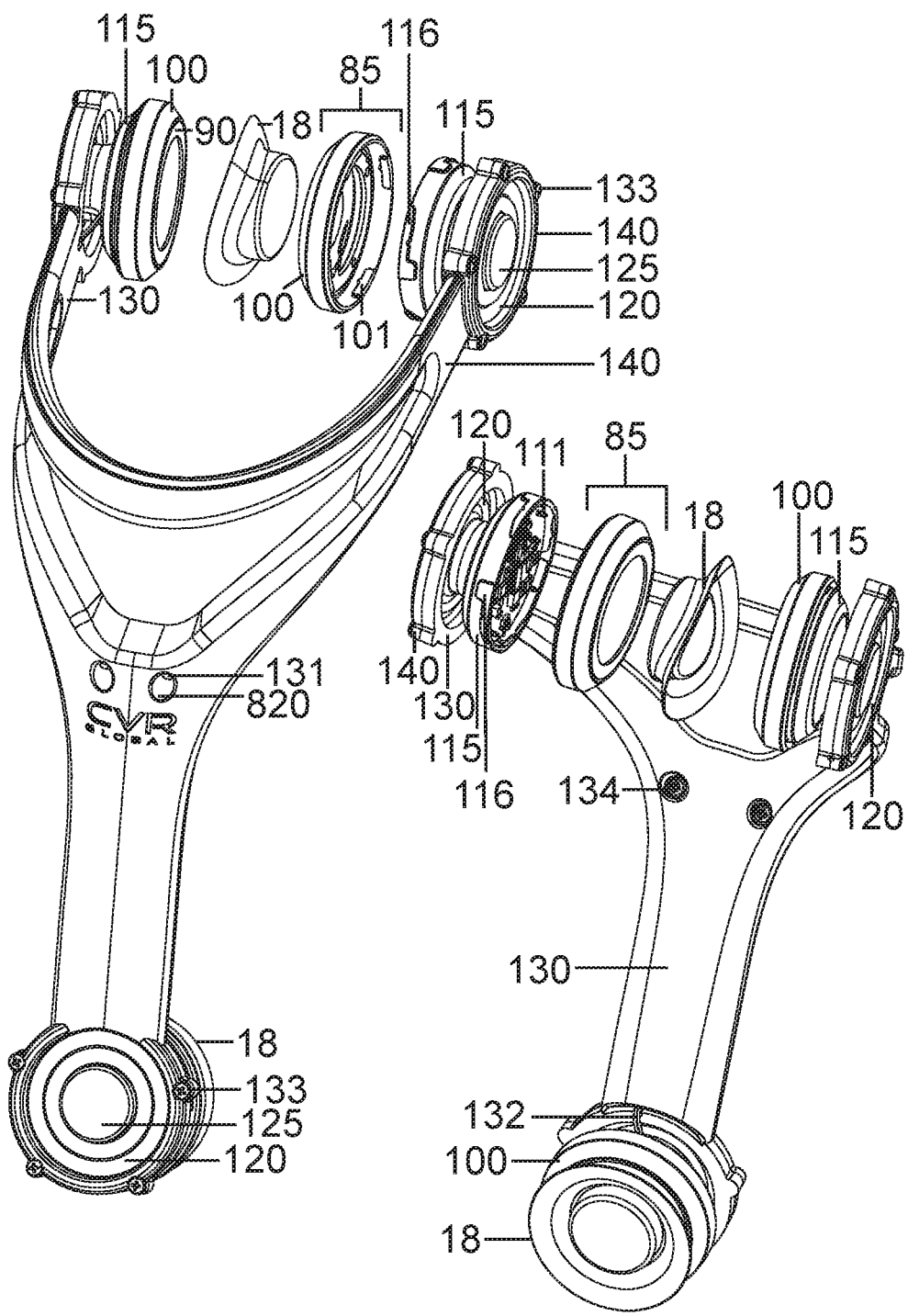
FIG. 1 depicts a partial exploded view of a sensor array and piezo pods.

As used herein, the term "a" "an" and "the" are intended to be singular or plural.

As used herein, the term "piezoelectric sensor" is used interchangeably with "piezo" or "Piezo sensor."

As used herein the term diaphragm bellows membrane is also referred to as DBM or a diaphragm.

Piezoelectric sensors have a variety of potential uses, but as described herein, they are being utilized as a contact microphone. The principle of operation of a piezoelectric sensor is that a physical dimension, transformed into a force, acts on two opposing faces of the sensing element. Detection of pressure variations in the form of sound is the most common sensor application, e.g. acting as a microphone, wherein the sound waves bend the piezoelectric material creating changing voltage. Accordingly, the piezo sensor can be placed on or near a sound to receive the sounds.

Piezo sensors are especially used with high frequency sound in ultrasonic transducers for medical imaging and industrial nondestructive testing. However, piezo sensors are also frequently used for the detection and activation of a device, based on the ability to receive a signal and to then send an electronic signal, thereby acting as the actuator. In the embodiments herein, piezoelectric sensors ("Piezo") are utilized for their ability to detect certain frequency sounds or vibrations caused by the distortion of a fluid flow vessel, specifically of the arterial circulatory system.

Because of the sensitivity of these sensors, piezoelectric sensors can be somewhat fragile and can be broken from both normal use and misuse. Furthermore, as utilized in a medical device, there is the inherent need to ensure accuracy of each of the three piezoelectric sensors. Accordingly, any slight modification of the sensor may result in a modification of the input received and thus would result in erroneous data.

Replacement components may be one of three different components as described herein. A first component may be a disposable piezo assembly, a second component may be a sensor pod, which comprises the disposable piezo assembly and a sensor base, and a third component may be a disposable array, comprising one or more sensor pods. In this manner, each component may be disposable to allow for easy replacement after use.

Piezo sensors can include any number of materials. Typically, however, the sensor contains a portion of ceramic material and a metallic component. Piezo sensors may also use a polymer film configuration which exhibits a low acoustic impedance similar to that of human tissue, or made of metallic materials. These sensors, as used in the invention herein, are typically a circular shape with a diameter of about 3 inches. Typical piezos have a diameter from about 0.01 to about 6 inches for use in medical settings, with most typical sizes between about 0.5 to about 4 inches in diameter. For most applications, including industrial settings, a range of 0.01 inch to about 12.0 inches is preferred, wherein the size of the piezo is generally related to the diameter of the fluid flow vessel to be measured. In preferred embodiments, the fluid flow vessels are veins and arteries in the body, for which a 4.0 inch or smaller diameter piezo is preferable.

There is no inherent frequency limit for a piezoelectric sensor. However, the limits of applications are usually determined by resonances associated with the shape and/or the size of the transducer design. The Piezo sensors utilized herein have a thickness of about 0.01 to 2.0 mm and are capable of detecting sounds between 10 Hz and 32 KHz and an amplitude of 0.0002 N/m2 to greater than 10 N/m2. In preferred embodiments, the piezos attached to a sensor pod detect sounds between about 20 to 3000 Hz, which are relevant towards measurements of fluid flow in the body. Typically, these sounds have an amplitude of between 0.002 N/m2 and 20 N/m2. While additional sounds are recorded, many of these sounds, i.e. the heart beat and extraneous noise, are removed from the data set through several filters.

FIGS. 17 and 18 specifically depict a new piezo and mount. The piezo 602 is a concave piezo, made of metallic or polymeric materials. Curved cap 601 contains an outer rim, and an inner flange adjacent to a central opening having a similar size and shape to the piezo. The flange supports the piezo 602 which can be engaged with an adhesive 603.

In the broadest sense, the piezo sensors are disposed of within a pod. On one side of the piezo is placed a sensor pad, for example those of 1, 2, 17 and 19. The sensor pad is then pressed against the skin or clothing of a patient to listen to the underlying circulatory system. The sensor pad allows for transmission of energy waves, sound and vibrations, which are received by the piezo element. Gel or other impedance matching substance may be applied to the skin facing surface of the pad.

Figure 6:
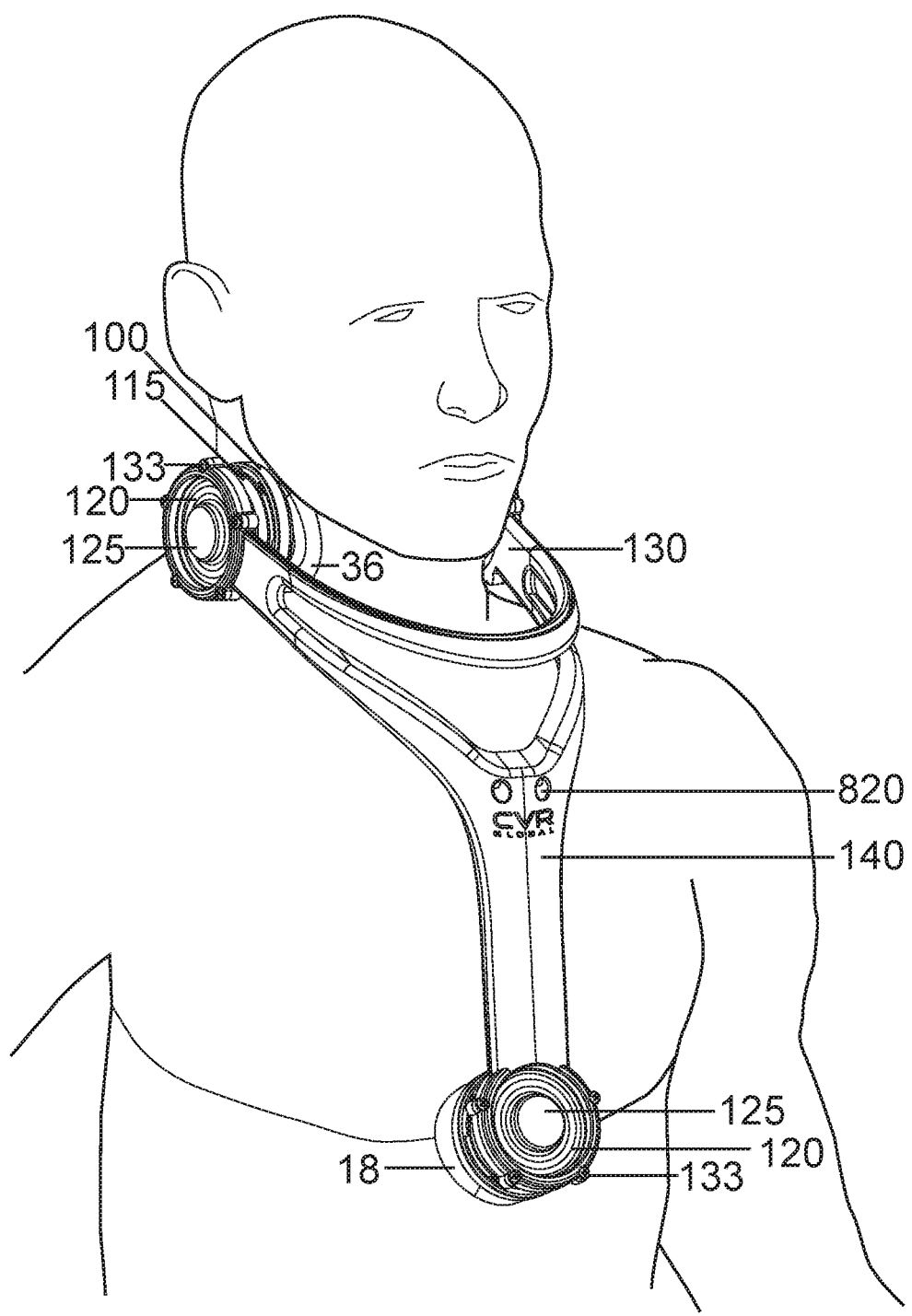
FIG. 6 depicts a sensor array on a person.

In view of FIG. 1, a sensor array is defined comprising a disposable sensor assembly 85, and a disposable sensor pad 18. These two features are replaced frequently, to prevent contamination and error. For example, the sensor can be placed on a patient as depicted in FIG. 6. The yoke 140, 130, and 3 is handheld by the patient during the test. Piezos wear over time and that damage can unfortunately occur from use. Because of the sensitive nature of the piezo, it is necessary to ensure that they are properly functioning before each use. Proper testing protocols utilize a program implemented through a computer, which generates a known set of sounds related to the sounds to be detected on the fluid flow vessel and matches the known played sound to the sounds detected and recorded in real-time by the sensor pods. Where the known sounds and detected sounds match, the sensor pod is confirmed to be working to specification. Wherein the sensor pod is not functioning properly, the system will sound an alarm, which will indicate to the operator the need to replace the disposable component. Accordingly, the piezos must be designed to allow for easy replacement of the piezo, while ensuring that the device maintains operation and reliability during ordinary use.

There are several ways in which the piezoelectric elements can wear or be damaged including ordinary and standard use of the device. Ordinary wear may occur as the piezoelectric element wears from ordinary and standard use, and after about 10 to about 400 uses, the piezoelectric element breaks down so that the function and the electrical currents generated are different when comparing the first use to the $2^{nd}$, $5^{th}$, $10^{th}$, $25^{th}$, $50^{th}$, $75^{th}$, $100^{th}$, $200^{th}$, $300^{th}$, or 400$^{th}$ use and all numbers in between. Accordingly, to ensure that accurate results are received by each of the units, it is imperative to replace the unit that has worn to maintain consistent results.

Additional wear or breakage can occur to the piezoelectric sensors by error or accident. For example, human error may lead to the array being dropped, or placed onto the base in a manner that breaks, bends, or otherwise damages the piezoelectric unit. Further damage may occur as clean sensor pads are attached and placed against the piezoelectric sensor for use on a patient.

To ensure sanitary use of the device, the sensor pads are replaced between each use of the device. However, because the sensor pads are placed directly onto the piezoelectric unit, there is risk that human error may damage the piezoelectric sensor, either by too much force, or simply through improper pressure applied to the piezo when installing or removing a sensor pad.

Ordinary wear or accidental damage is tested through routine quality control procedures performed in a self-diagnosis module. The sensor pods can be placed in a base or holding device that comprises a speaker embedded within the base which provides a predetermined sound that can be measured by each piezoelectric sensor. When the sensor device is activated for use, the sound, which can include both audible and inaudible sound waves, is played for between about 1 and about 20 seconds. During the time that the sound is playing, each of the piezoelectric sensors records the sound and a program then confirms that each of the three sensors is recording the appropriate sounds being played. If each of the three sensors detects the appropriate sounds, then the sensor device is ready for use. However, if one or more of the sensors detects sounds that do not match with the predicted sounds, the device will provide an alert, which may include lights, sounds, or other display elements, to alert the user of the device that one or more of the piezos needs to be replaced.

An optional display screen attached to the base can further display the device and identify the sensor pod containing the piezo that failed the QC test. Another manner for identifying the failed sensor is to have lights that correspond to working or failed tests either on the base or on the sensor array itself. Once the failed piezo is identified, the user can then replace one or more of the components, as described herein, and then perform the QC test again to ensure that the device is now ready for use.

Accordingly, in a preferred method, a piezo is replaced every 10 uses to ensure that there is no noticeable wear and tear on the piezo, and to prevent the possibility of erroneous data. Accordingly, the sensor device comprises a counter wherein the number of times that a test is run with each of the piezo is counted, so that the sensor device notifies a user that the piezo needs to be replaced, even if each of the piezos are working properly.

In other embodiments, the piezos can be replaced every 1, 2, 5, 10, 25, 50, 75 uses, 100 uses, 125 uses, 150 uses, about every 200 uses, or about every 400 uses or a number in-between. The particular number of uses for each piezo will be determined through additional use of the devices in normal practices. However, to ensure sanitary and consistent results, it is preferred that the piezos are changed after no more than 100 uses.

To facilitate easy changing of the disposable piezo assembly 85, the disposable piezo assembly 85 is able to easily attach to an underlying disposable sensor base 86, and to be replaced. For example, a simple threaded attachment mechanism allows the sensor pod to be removed from the sliding sensor pod base, which is attached to the sensor array. Alternatively quarter, or half-turn attachment means, magnetic attachment, and others as known to one of ordinary skill in the art are known.

FIG. 1 depicts a sensor array comprised of an inner array half 130 and an outer array half 140. The halves are secured together with threaded fasteners 134 and 133, though adhesives, snap fits, or plastic welding can be utilized for securing means. At the bottom of the array is a first sensor pod, depicting a locking cap 125 and a DBM 120 with a sensor pad 18 positioned on the obverse side, with a threaded fastener 133 securing said membrane in place. The DBM 120 is an elastomeric member, with or without articulating bellows geometry, containing an inner opening and an inner and outer flange, suitable to secure the DBM to an array, and to allow for the sensor pod to move freely on said array. The DBM 120 may also be attached to 130 or 140 via insert molding.

Near the vertex of the Y is a charging port, 820, and a PCB charging contact 131 disposed therein. This allows the array to be placed into a charging port and charge a central battery.

Attached to the array is a sensor pod, made up of the components of a locking cap 125, a DBM 120, a PCB processor board 110, a PCB housing 115, a piezo cap 100, a piezo 90, and a disposable piezo assembly 85. These features are further detailed below. A disposable sensor pad 18 can be affixed to the piezo 90 via adhesives or by the natural adhesion of the pad material. For example, the piezo cap 100 can be attached to the PCB housing 115 in several ways, including as in FIG. 1 with a quarter turn feature, comprising a recess 101 and a locking feature 116 having corresponding openings to the pins on the piezo cap 100. By securing these together, the spring pin 111 is engaged and provides electrical contact between the components to power the piezo 90 from an internal power source. Features 101 and 116 can be swapped, provided they are maintained as a matching pair, to allow for selective attachment and detachment of the disposable piezo assembly 85. A recess is provided in the top of the piezo cap 100 for mounting the piezo 90 via pressure sensitive adhesive 92. The recess contains a flange which supports the circumference of the piezo 90 within the piezo cap 100. This recess also allows the piezo to sit about flush with the top of the piezo cap 10, for placement of the sensor pad 18.

Figure 2:
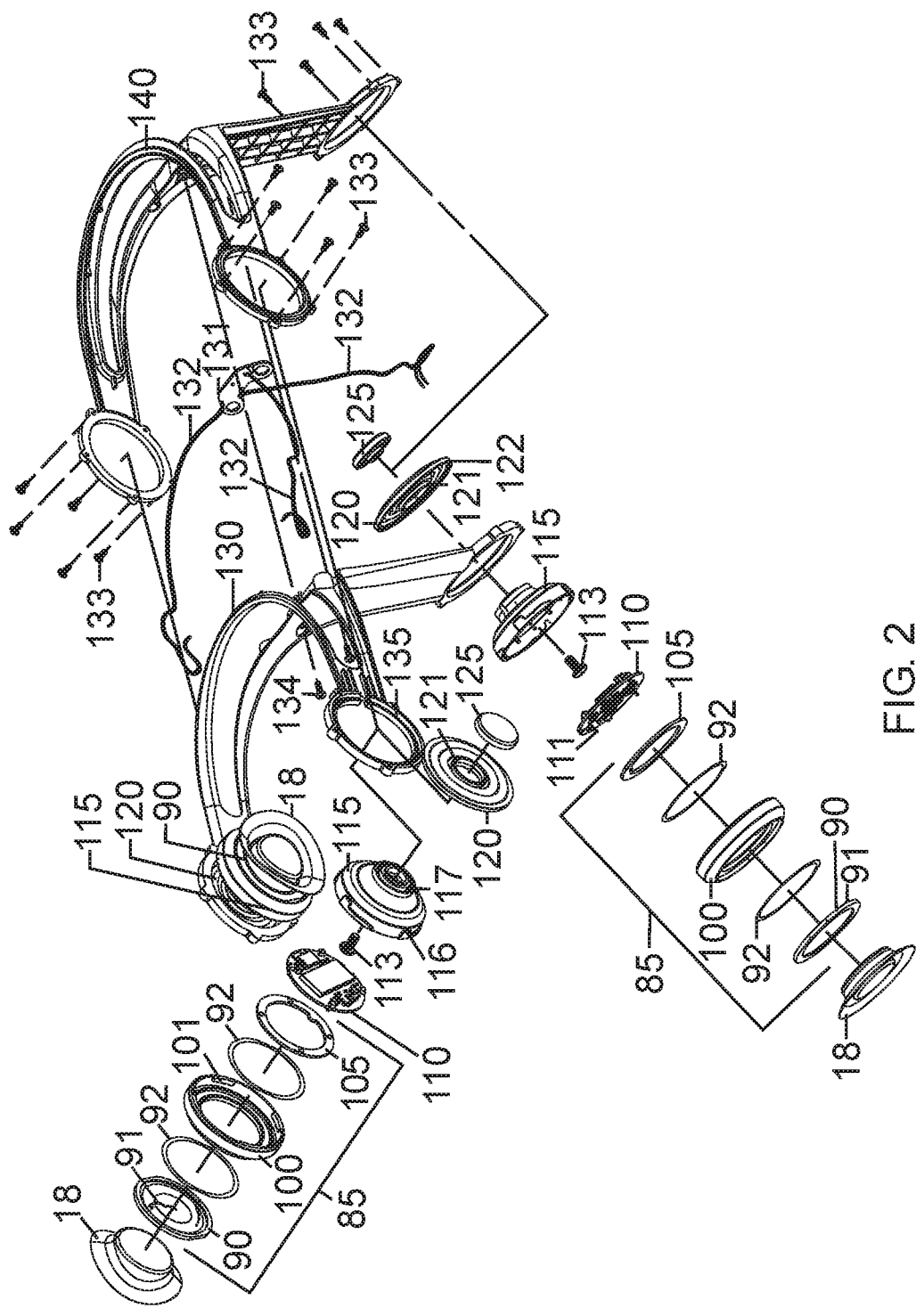
FIG. 2 depicts an exploded view of a sensor array and piezo pods.

FIG. 2 provides a further exploded view of FIG. 1. A disposable sensor pad 18 is provided to be attached to the disposable piezo assembly 85. The assembly 85 comprises a piezo wiring 91 which connects the piezo 90 to the PCB contact board 105. Two pressure sensitive adhesives 92 are provided, one connecting the piezo 90 to the piezo cap 100 and another adhesive 92 connecting the piezo cap 100 to the PCB contact board 105. These components make up the disposable assembly 85.

In one embodiment, this disposable assembly 85 is the smallest disposable component, which allows for quick and easy replacement of the piezo without replacement of any further components (except for the disposable sensor pad 18, which is replaced for every use). The disposable assembly 85 comprises a quarter turn locking feature 101 that corresponds to a paired feature 116 on the PCB housing 115. This allows for a small turn of the disposable assembly 85 to remove the component and replace. Additional attachment mechanisms can be easily exchanged, for example magnetic, threaded engagement, or simply a threaded fastener or two that can be engaged for replacement. Finger capable fasteners can use a full, half, or quarter twist to secure a fastener between two components. A person of skill in the art will recognize that numerous options exist for attaching and detaching such components and that attaching means incorporates these listed and additional options not described in detail herein.

The PCB housing contains a locking groove 117 that engages with and locks the elastomer DBM 120 to the PCB housing 115. In particular locking groove 117 engages locking key 121 between the locking cap 125 and the PCB housing 115. A locking cap 125 engages to a fastener 113 to secure the key 121. A second key 122, is also provided to lock the DBM 120 between the outer array housing 140 and the inner array housing 130. A further detail of these locking features are provided in FIG. 7.

While the disposable assembly 85 can be easily removed and replaced, it is also contemplated that the entire sensor pod can be removed and replaced easily. For example, removal of threaded fasteners 133 will allow for quick and easy replacement of the entirety of the pod, inclusive of the DBM 120. Furthermore, the DBM 120 can be held in place, and the locking cap 125 can reveal a threaded fastener 113 to replace the remaining components. In the FIG., the fastener 113 can be oriented in either direction to allow for quick replacement.

FIG. 2 further details components of the array including a PCB charging contact 131, connecting a wiring harness 132 to each of the piezo sensors 90. A battery, not depicted, can be positioned within the array handle to power the devices, or can be attached directly to an AC or DC power source with a wire.

Figure 3A:
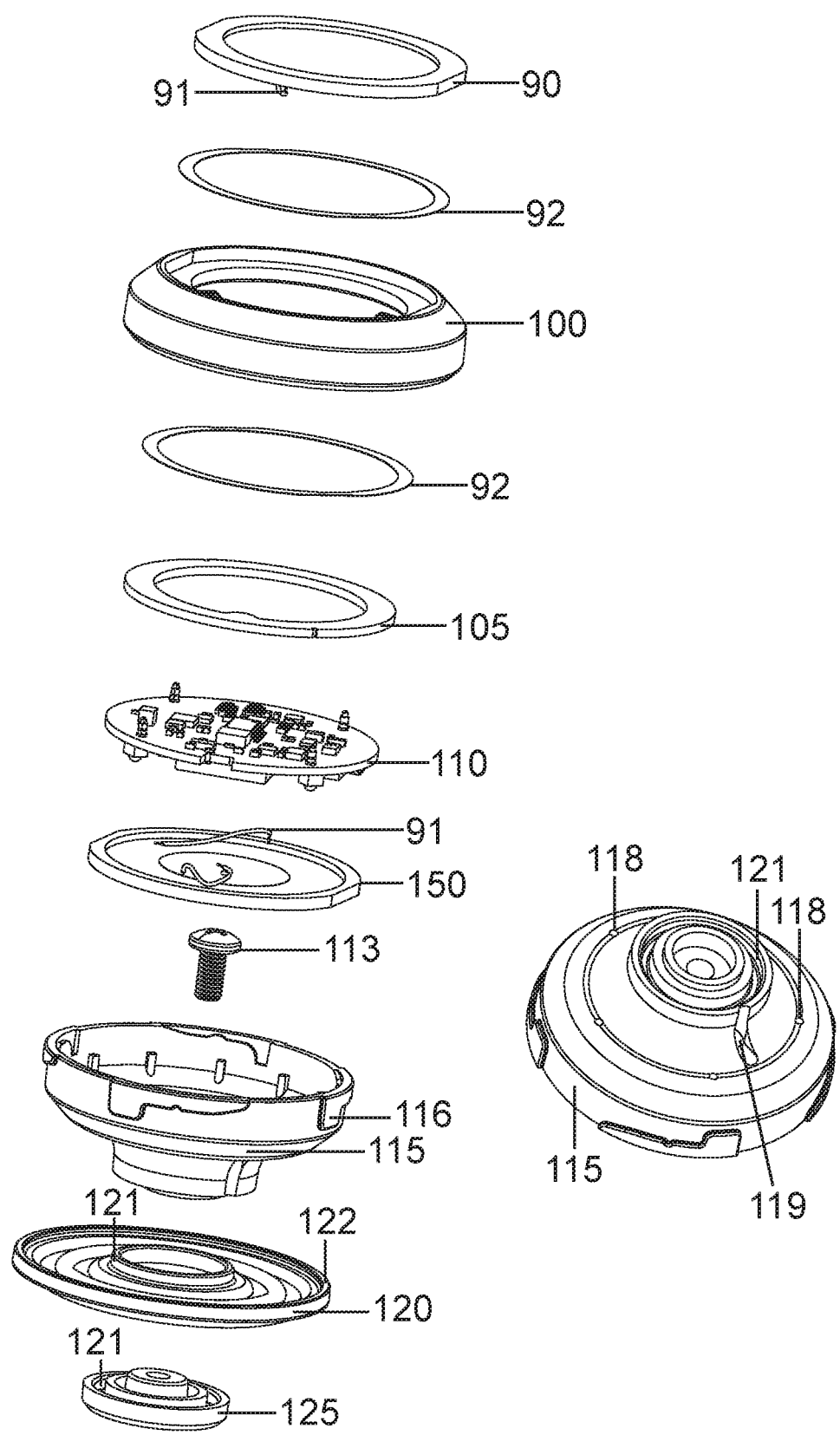
FIGS. 3A and 3B depict an exploded view of a piezo pod with bellows membrane.
Figure 3B:
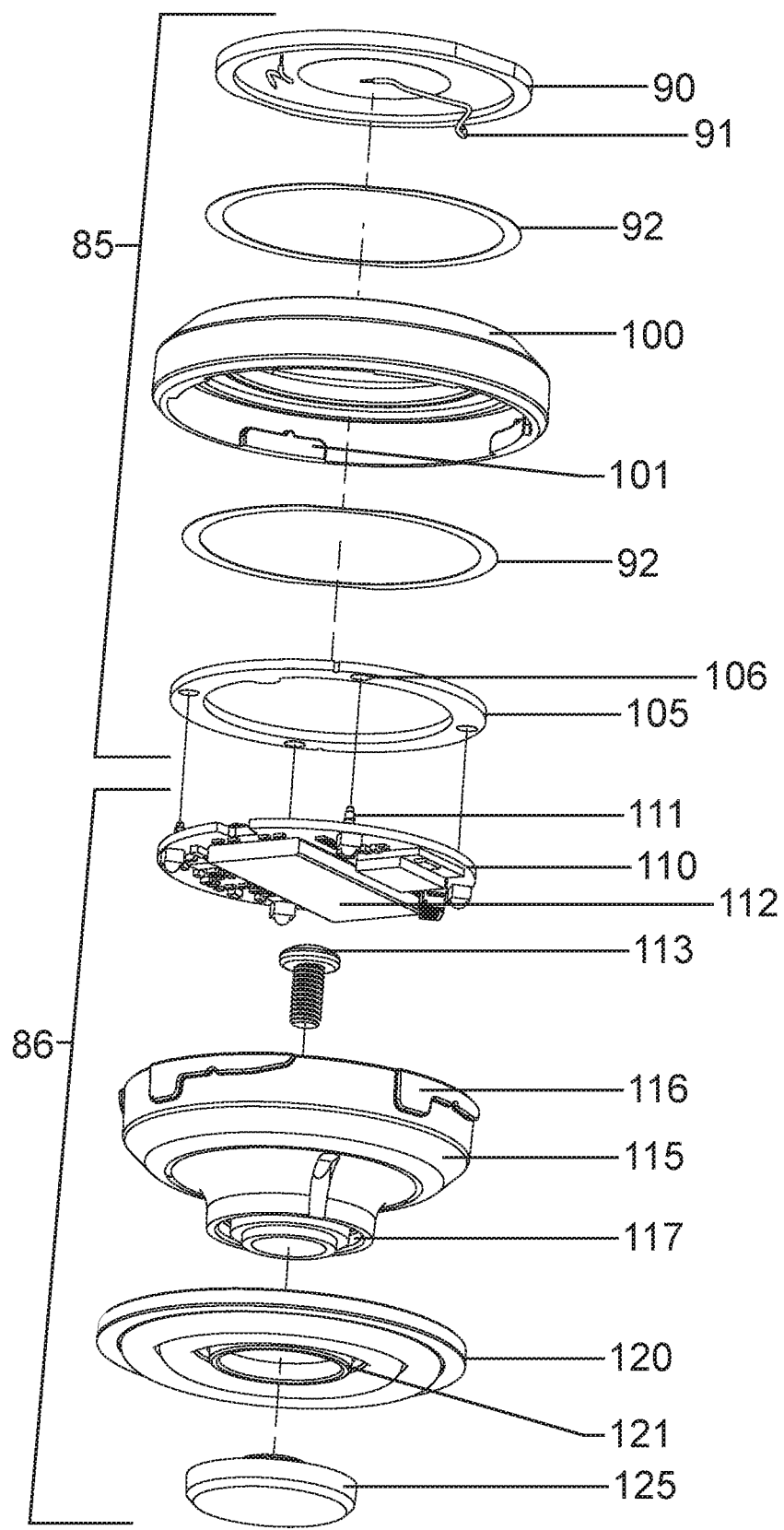

FIGS. 3A and 3B depict further exploded views of a sensor pod. FIG. 3A specifically defines a dual piezo mechanism, wherein a second piezo 150 is attached to the rear of the PCB processor board 110 to allow for noise cancelling. Briefly, though described above, FIG. 3A depicts a piezo 90 a pressure sensitive adhesive 92, a piezo cap 100. The adhesive 92 engages the flange of the cap 100, and said flange supports the piezo 90 at its circumference. A second pressure sensitive adhesive 92 is positioned inside of the piezo cap 100 and engages to the PCB contact board 105, which contacts a PCB processor board 110. A second piezo 150 is engaged on the rear of the PCB processor board and a wiring 91 attaches the piezos to the PCB processor board 110. A threaded fastener 113 secures the PCB housing. The detail of the locking features 121 and 122 are best seen in a later figure. Sound locking holes 118 are depicted as well as the entrance hole 119 for the wiring harness 132.

FIG. 3B depicts a single piezo 90, a piezo wire 91, the adhesive 92. These combine into the piezo cap 100, which contains a locking feature 101. The second adhesive strip 92 attaches to the PCB contact board. The spring pin 111 is seen positioned to contact the PCB contact 106. A battery 112 is attached to the PCB board 110. A screw 113 attaches the PCB housing to the locking cap 125, which secures the DBM 120. The disposable piezo assembly 85 is combined with the sensor base 86 to form a sensor pod. Each of the disposable piezo assembly 85 and the sensor base 86 are replaceable or disposable, as needed.

Figure 4:
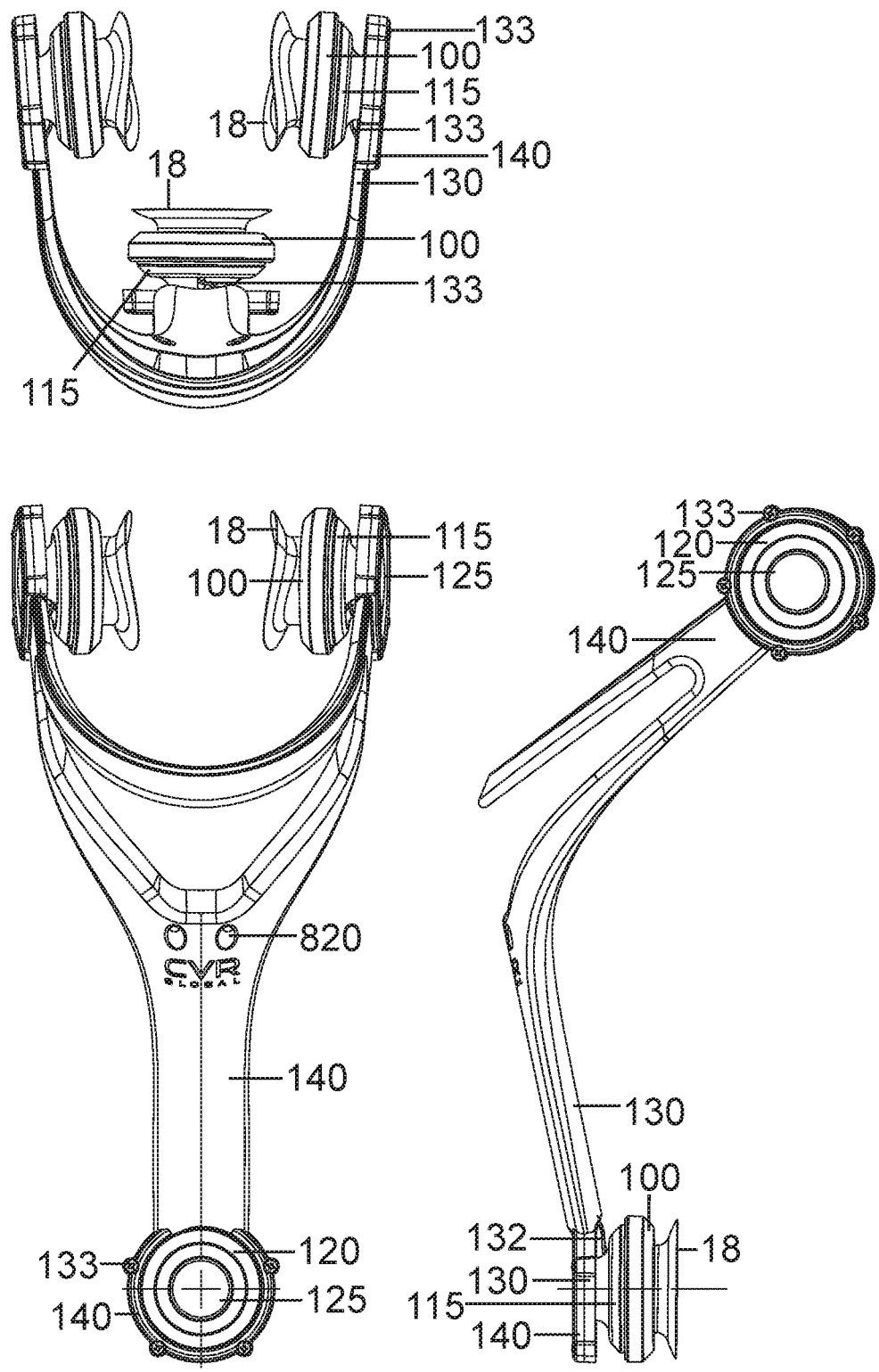
FIG. 4 depicts various views of a sensory array with piezo pods attached.

FIG. 4 depicts several views of an array, with an angled sensor pad 18 positioned on each of the different sensor pods.

Figure 5:
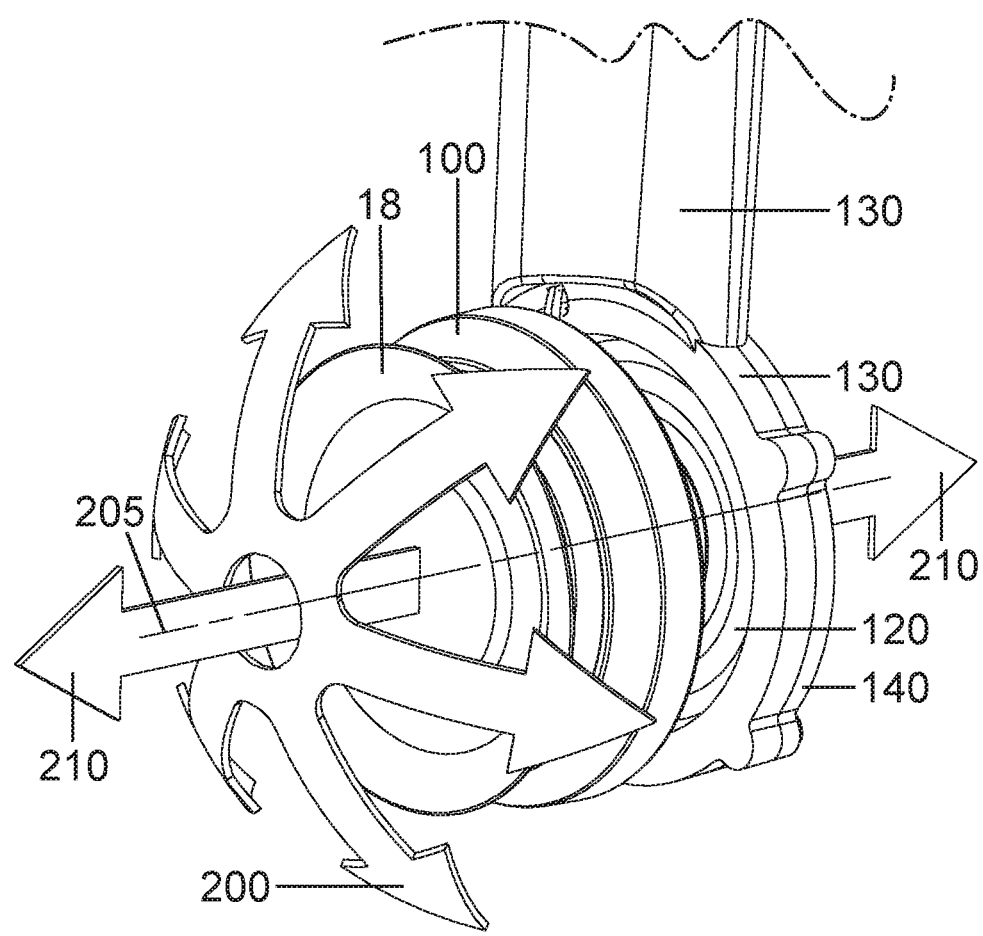
FIG. 5 depicts the movement of a bellows membrane on a piezo pod.

FIG. 5 depicts the possible movement of the DBM 120. The arrows 200 refer to spherical movement of the entire assembly, including the sensor pad 18, and the disposable piezo 85. The centerline 205 is provided, with all features moving in the direction of 210, both forward and backward, as necessary. In this manner, the DBM 120 allows for the entire feature of the sensor pad 18 and piezo 90 to press against a surface and extend away from the surface, but to return back to a central position after use. Furthermore, the spherical movement 200 allows for angular rotation to rotate and angle the sensor pad 18 to best fit against the skin surface of a patient, for example as depicted in FIG. 6. Here, a different sensor pad 36 is used against the skin surface on the neck, as compared to the sensor pad 18 at the torso. Appropriate pads, having different shapes can be used based on the needs of the particular patient.

Figure 7:
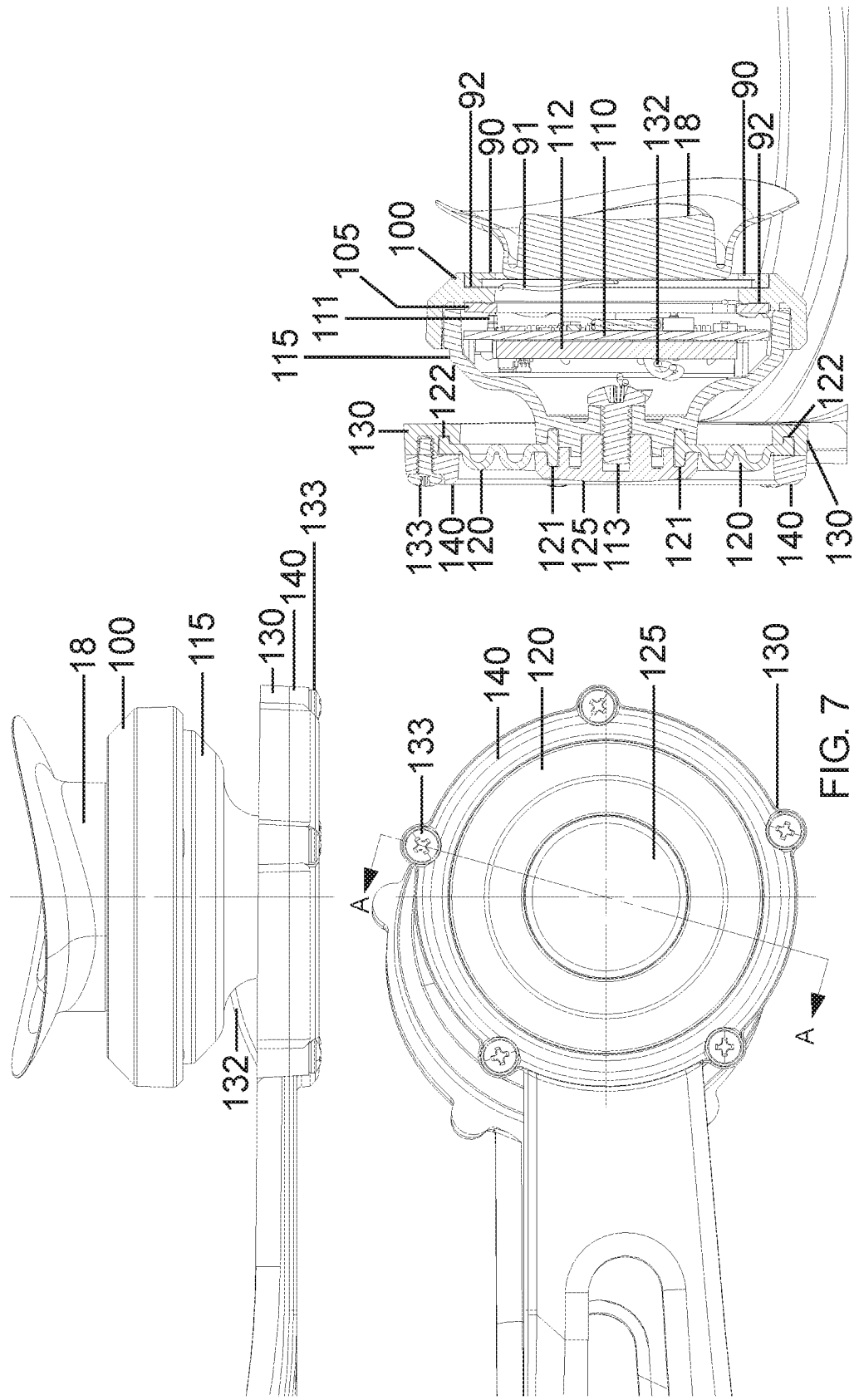
FIG. 7 depicts a side and sectional view of a bellows piezo pod.

FIG. 7 depicts a side profile and cross-sectional view through line A-A, of a sensor pod with DBM 120. The side profile shows a sensor pad 18 positioned above the piezo cap 100, PCB housing 115, the wiring harness 132 and the inner array 130 and outer array 140 connected with threaded fasteners 133. The cross-sectional view depicts a PCB housing 115 engaged to the Piezo cap 100, with the adhesive 92 securing the piezo 90 at the right hand side. The left hand side depicts the inner array 130 secured to the outer array 140 with a fastener 133. By compressing these together, the elastomer DBM 120 is compressed together. For example the locking feature 122 is depicted securing the edge of the membrane 120 between the inner array 130 and the outer array 140. The inner locking feature 121 is secured between the PCB housing 115 and the locking cap 125. A fastener 113 is provided therein. Each side is similar through the cross-sectional view.

The DBM 120 is a circular feature having an inner opening. At the outer edge of the DBM 120 is an outer flange 122. At the circumference of the inner opening, there is an inner flange 121. These flanges 122 and 121 are used to lock the DBM 120 into place between the array features 130 and 140, as well as between the locking cap 125 and the housing 115.

Therefore, the DBM 120 is an elastomeric material, capable of allowing the attached piezo to flex in any direction, as well as move away from the surface to be compressed. This allows for a consistent pressure to be applied to the skin surface by the sensor pad 18, based on the rigidity of the membrane 120.

Figure 8:
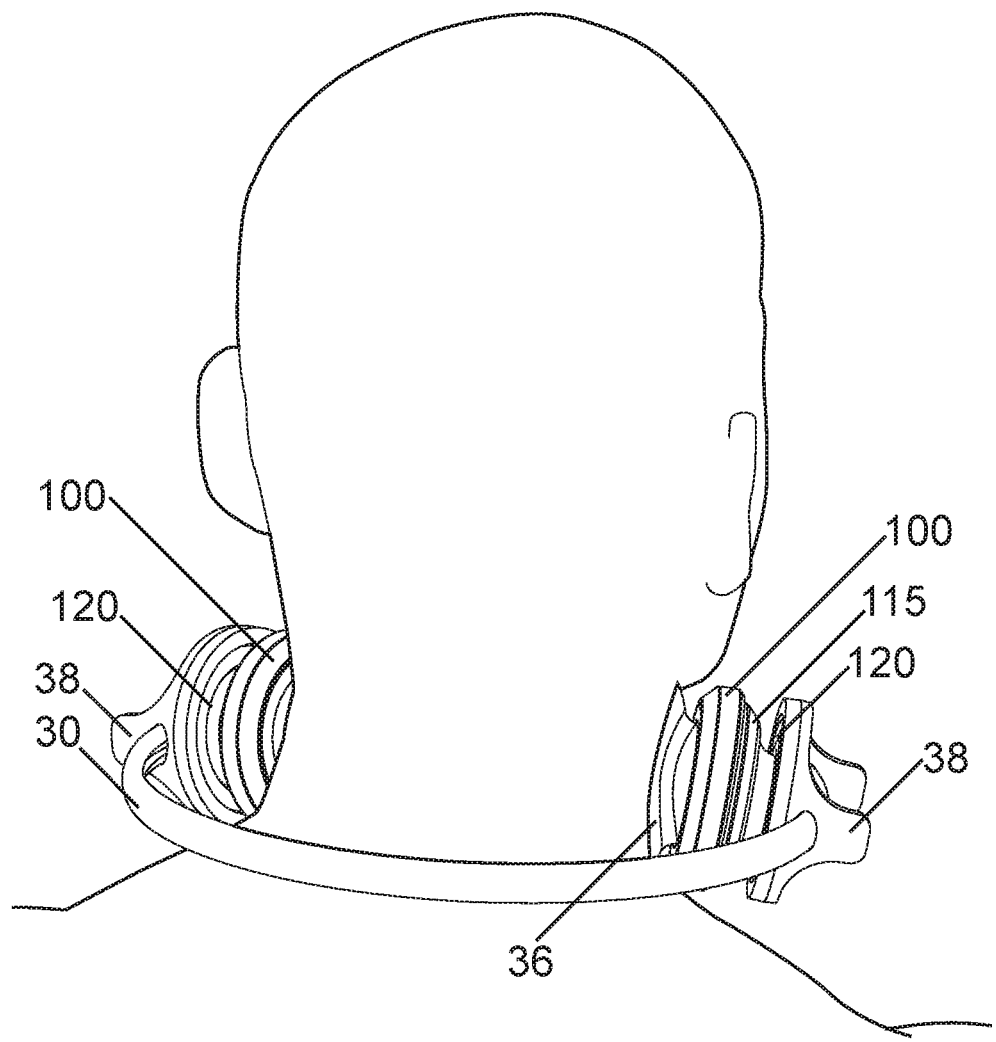
FIG. 8 depicts a rear neck sensor array and two attached slideable sensor pods.

FIG. 8 depicts a rear image of a neck array 30. Threaded on the neck array 30 is a piezo base 38 comprising openings to allow for movement along the neck array 30. Attached to the piezo base 30 is a DBM 120 as depicted in part of FIG. 7, with the difference being features 130 and 140 are exchanged for the components of the piezo base 38. The neck array 30 is a track-like structure, about which the sensor pods can slide on openings in the piezo base 38. The neck array 30 is generally "C" shaped, and when the sensor pods are at the end of the track, are oriented for placement on the carotid artery. However, the sensor pods can be centrally aligned, thus being side-by-side and placed together on an area of interest.

Figure 9:
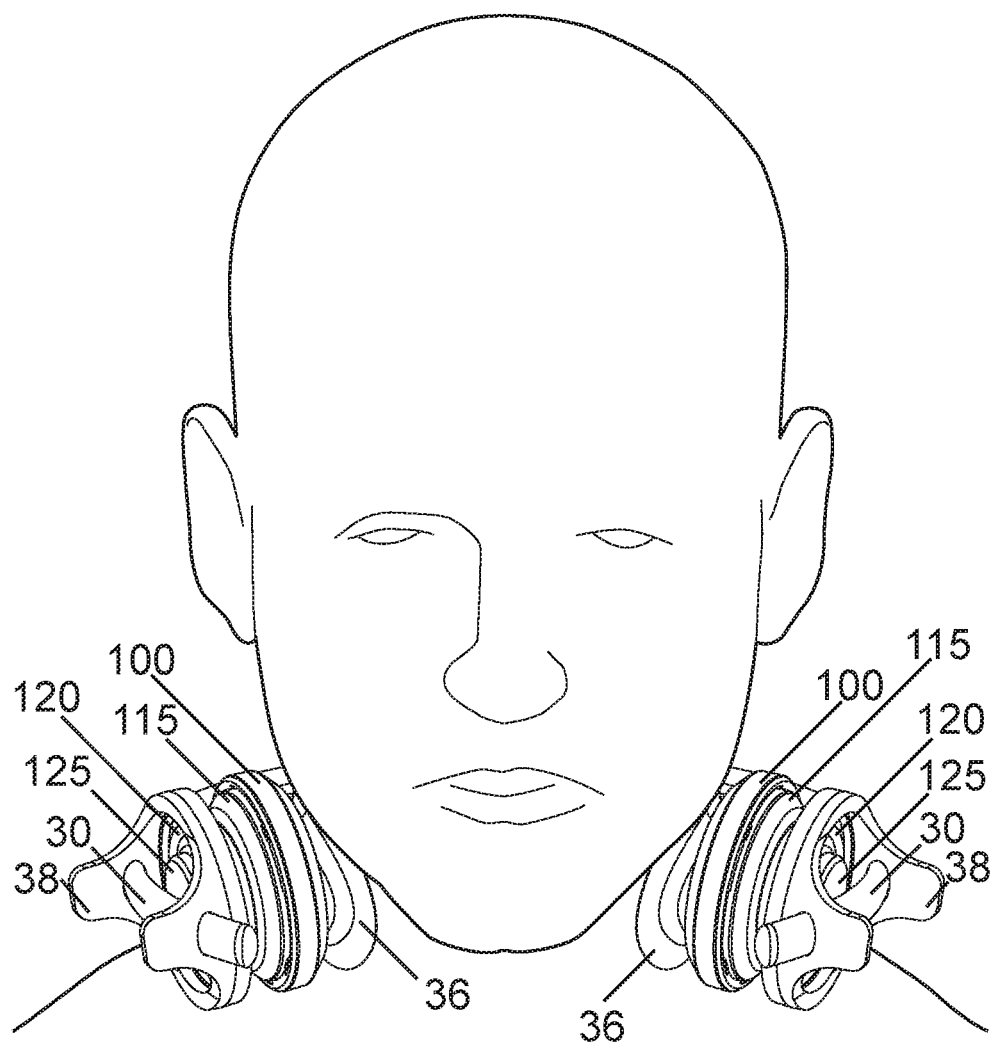
FIG. 9 depicts a front view of a rear neck sensor array and two attached slideable sensor pods.
Figure 10:
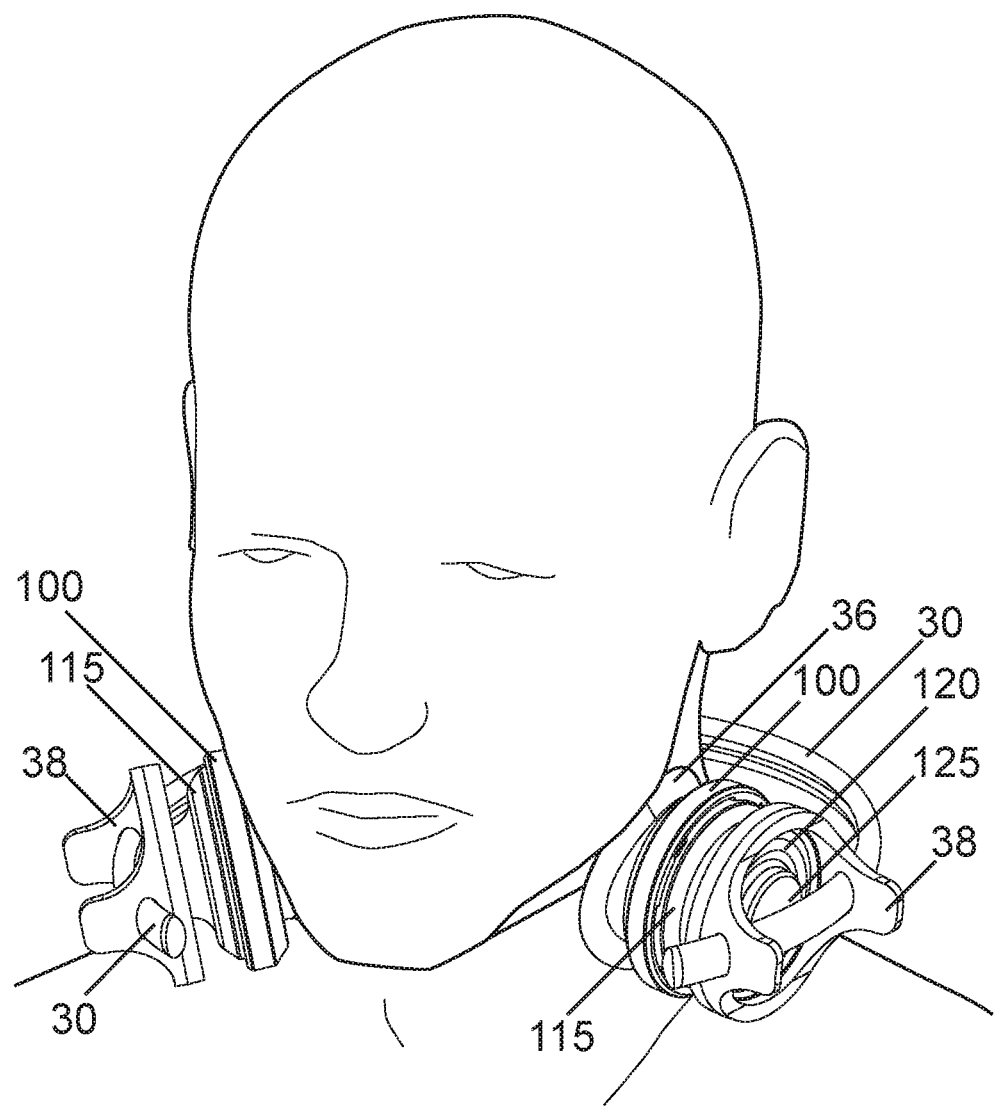
FIG. 10 depicts an alternative view of FIGS. 8 and 9.

FIG. 9 depicts a front view of the neck array 30, which more particularly depicts the piezo cap 100, the sensor pad 36, the PCB housing 115, the DBM 120, the locking cap 125. FIG. 10 provides an alternative view of FIGS. 8 and 9.

Figure 11:
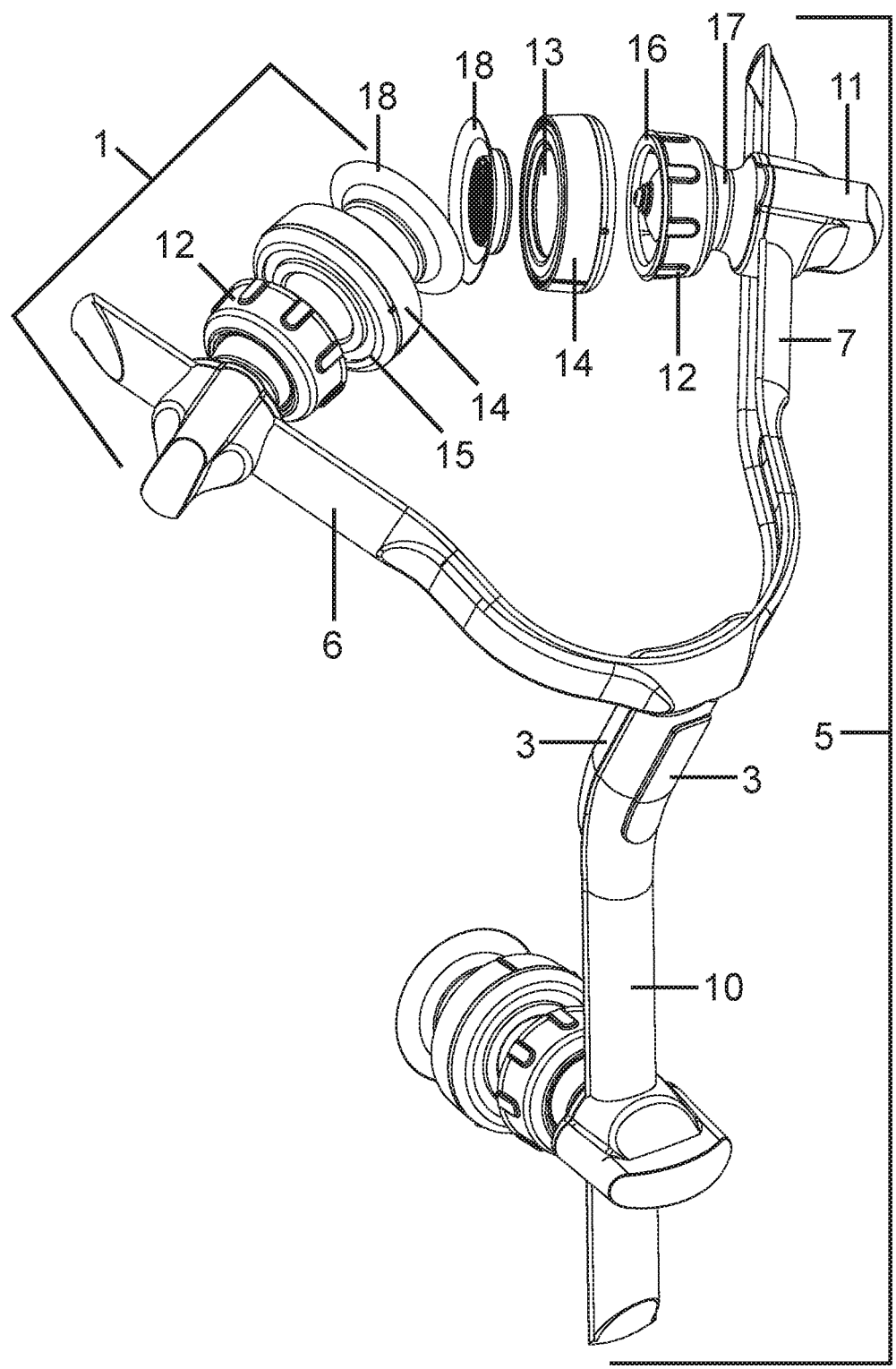
FIG. 11 depict an alternative sensor array and sensor pods secured on the array, with a partial exploded view of certain disposable components.

FIG. 11 depicts a variation of an array 5, having a stem 10, a left arm 6 and a right arm 7. Like the neck array 30, this embodiment of an array, comprises a pod sled 11, which allows the sensor pods 1 to move along the arms 6 and 7 or the neck 10, to allow for fit of these sensor pods 1 on a patient. A rear pod mount 12 comprises attachment means 16 which secures to the piezo cap 14. For example, the attachment means 16 may be a quarter thread, pin and recess. Alternative is a paired threaded fastener, a set of magnets, threaded fasteners having an opening in one end and threads in the other. A piezo 13 is depicted at one end, and the sensor pad 18 can be placed on said piezo. Rotation of the rear pod mount 12 will remove the piezo cap 14 and included piezo 13. Alternatively, the pod sled 11 can be rotated in a quarter, half, or full turn to separate from the sled ball 17, and remove the entire part of the sensor pod 1 or be attached with mechanical fasteners 415. Accordingly, easy removal is possible for either just the disposable piezo component 13, or for the entirety of the sensor pod 1, by removal of the pod sled 11.

In an ideal world, every patient would be the same shape and size, and modification of the structure would not be required. However, in practice, men, women, and children have significantly different shapes and sizes due to the amount of body mass, muscle, breast tissue, fat deposits, etc. Specifically, changes in body mass and shape between the neck and the torso create issues where the array must be modified to position one or more sensors in appropriate positions for acoustic sensing.

Therefore, as used on human patients, a difficulty in such devices is that people come in all shapes and sizes and that the array must be easily modified to fit these different shapes and sizes. One option would be to utilize different sized, fixed position sensing elements, due to the fragile nature of the sensing elements. However, constant movement and replacement of the sensing elements from one device to another would likely result in more damage to the sensing elements and increase the risk for the need for frequent replacement of these elements. Therefore, an array with rails, both the neck and "Y" versions, provides the necessary stability and flexibility provides a great advantage in the array for use on patients.

A particular feature of the sensor pods when affixed to an array is that they are adjustable and can be configured to account for the anatomical differences between individuals while remaining sufficiently rigid to support the sensing elements. Such flexibility can be seen in the depiction of FIG. 5 or in the angled pod, in FIG. 12.

Figure 12:
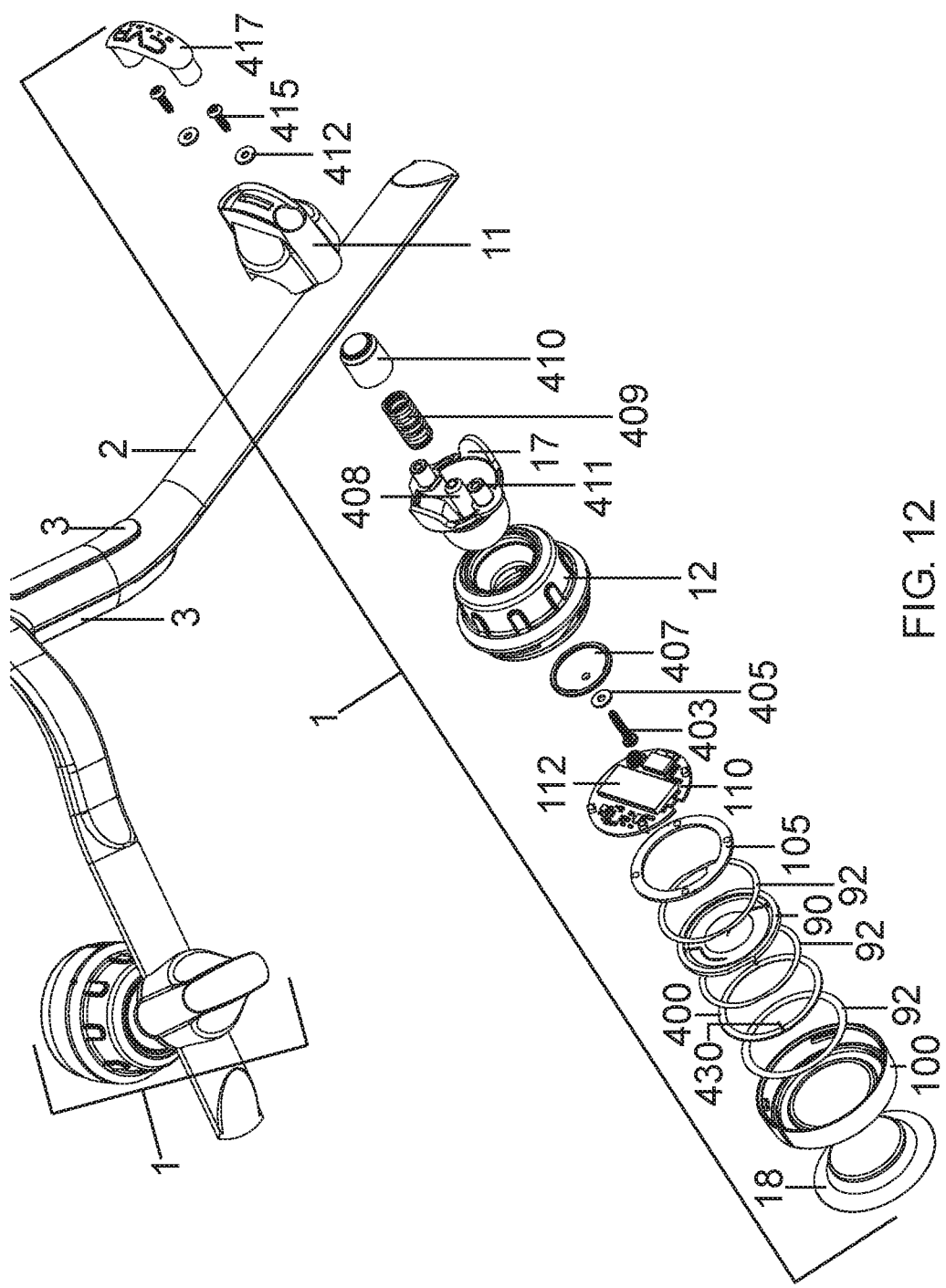
FIG. 12 depicts an exploded view of a sensor pod having sliding means on an array.

The exploded view of FIG. 12 details a variation of a sensor pod 1, showing the components that make up the sensor pod 1 able to slide along the array. The sensor pad 18 attaches to the piezo 90 via adhesives or the natural adhesion of the material. Within the piezo cap 100, receiving charging coil 400 attaches to inside of 100 with a pressure sensitive adhesive 92. Piezo 90 attaches with pressure sensitive 92 receiving charging coil 400. PCB contact board 105 attaches via pressure sensitive adhesive 92 to piezo 90. The receiving charging coil 400 makes electrical contact with the PCB contact board 105 with a soldered or crimped connection along wires 430. A PCB processor board 110 is then compressed adjacent into 12 and makes electrical connection via spring pins 111 to PCB contact board 105. The sensor pad 18 fits within the piezo cap 100, which is attached to a pin board 400 with a pressure adhesive 92. Another adhesive connects the board to the piezo 90, and another adhesive connects this to the PCB contact board 105. A fastener 403 with a washer 405 compress with a friction washer 407 into the knuckle 12. A sled ball 17 allows rotation of the piezo when mounted, held, in part, by the friction of the knuckle 12 and the friction washer 407. A spring 409 compresses against spring cap 410 and sled ball 17 when pod sled 11 is assembled to sled ball 17 via washers 412 and threaded fasteners 415, creating frictional pressure against the inside surface of array arm 2. This allows for very easy positioning of the pod assembly 1, anywhere along array arms without actuating any mechanical buttons. Fasteners 415 can be excluded for attachment means, such as quarter-turn, half-turn, full-turn threaded attachment, magnetic, or other similar attachment means, to allow for easy removal of the sensor pod. Alternatively, the sensor pods can simply slide off of the end of the senor, and a new one replaced by sliding it into place. The spring 409 holds the sensor pod into place during use.

Figure 13:
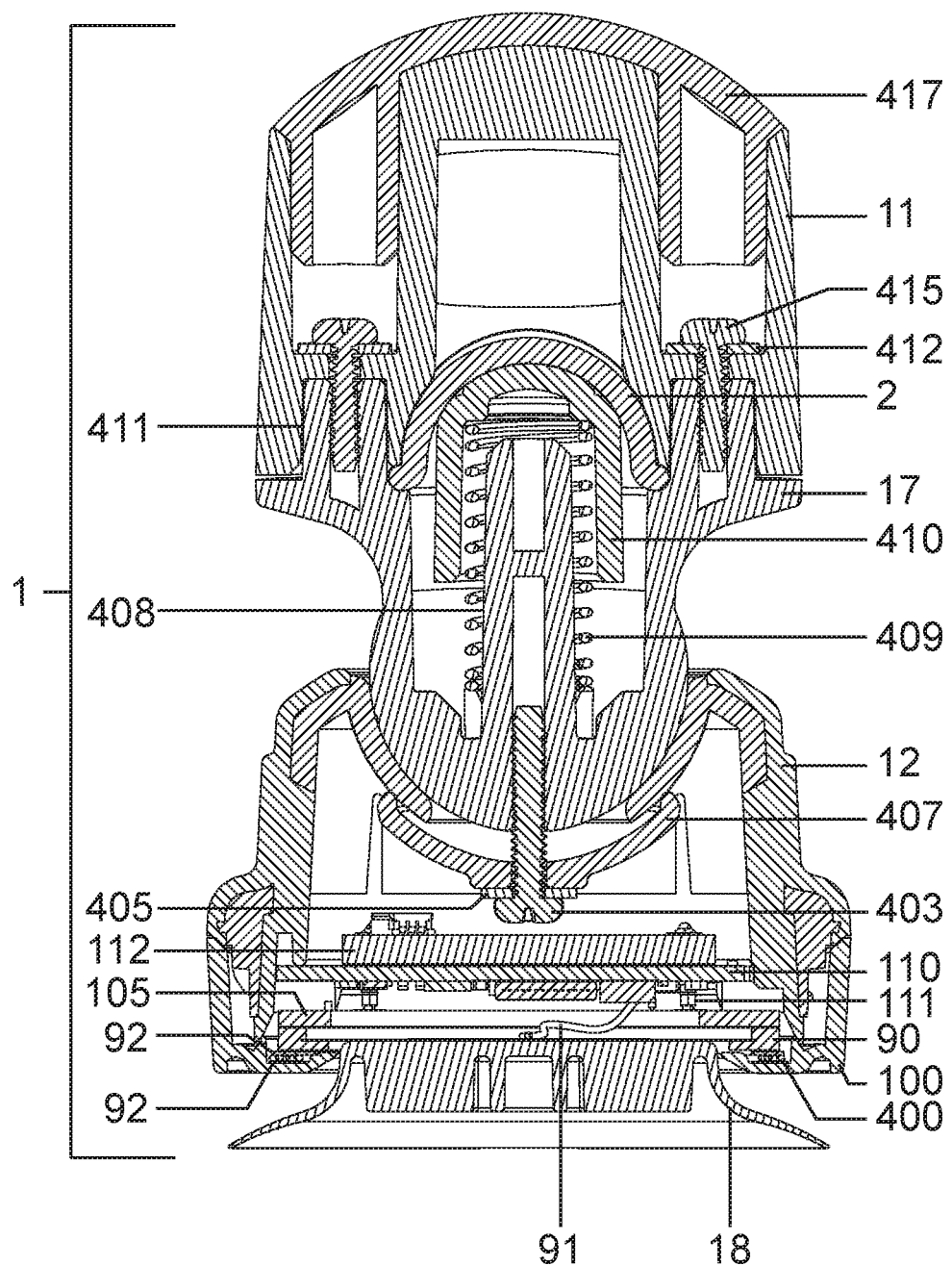
FIG. 13 depicts a cross-sectional view of a slideable sensor pod.

FIG. 13 depicts a cross-sectional view of FIG. 12.

Figure 14:
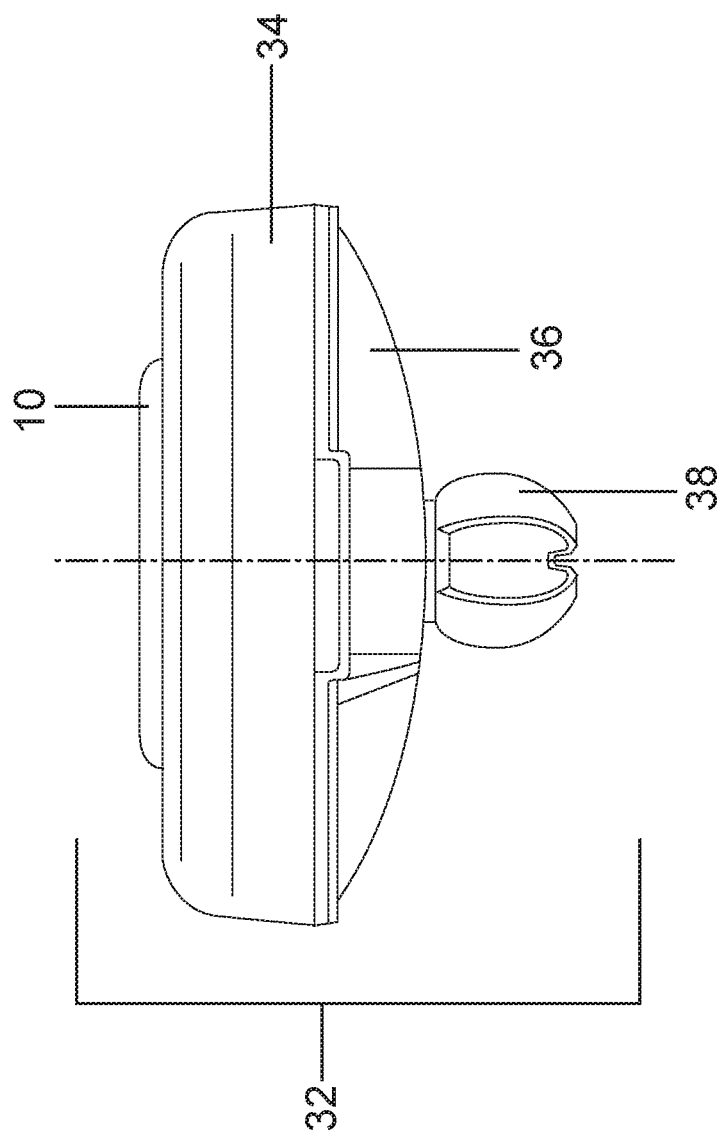
FIG. 14 depicts a disposable sensor pod with pin mount.

FIG. 14 depicts a sensor pod having a pin mount 38. This pin mount can engage to a ball mounting system, to allow for rotation of the sensor pod. A corresponding ball recess can be provided to allow for such attachment means and rotation. The fastener acts as a ball and socket, allowing rotational movement.

Figure 15:
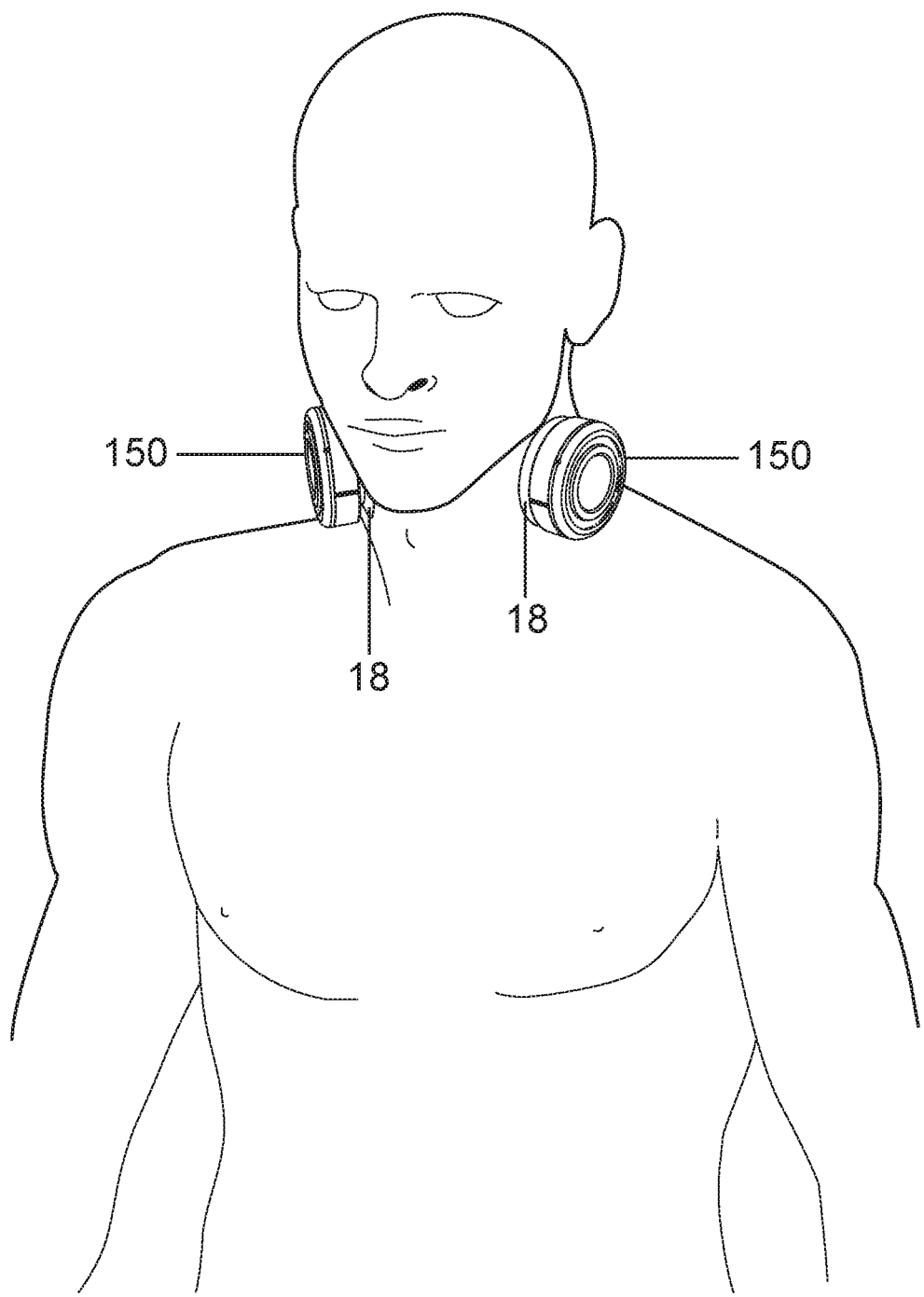
FIG. 15 is a view of two piezos without an array.
Figure 16:
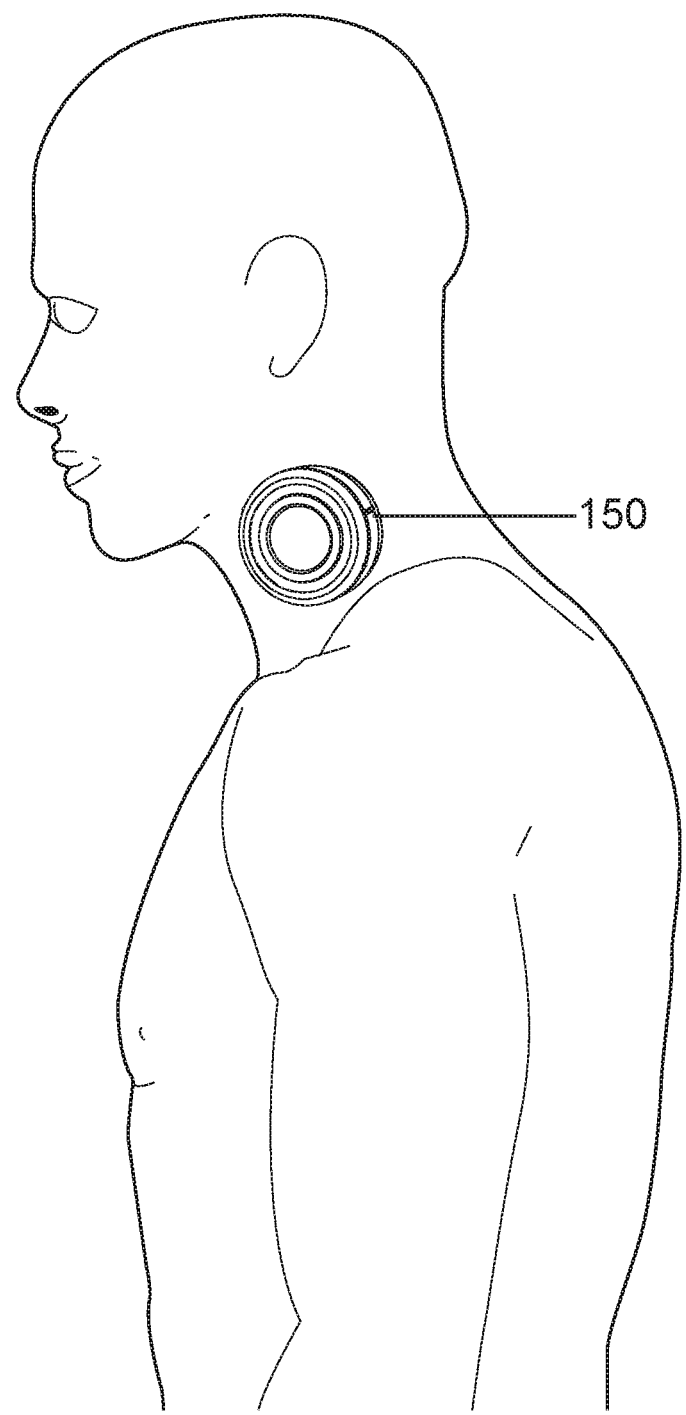
FIG. 16 is a side view of a piezo without an array.

FIGS. 15 and 16 depict a piezo pair that does not utilize an array. Accordingly, the piezo 150 relies upon an adhesive surface on a sensor pad 18 to allow the piezo to stick to the skin surface. In certain embodiments, it is advantageous to perform a test with one piezo at a time, with the patient laying in a position to allow for the piezo to rest with gravity. Thus, the adhesive does not need to be so strong but rather merely sufficient to hold the piezo into a relatively stable position. This may be useful for situations where an array is impracticable, whether due to the dimensions of the patient, surgical procedures, or the like, that would restrict access of an array. Furthermore, by eliminating the array, a further source of noise may be eliminated from the data sample.

FIGS. 17 and 18 depicts a gel pad with cylindrical surface 600 that contacts with the piezo film 602. The upper frame 601 supports the piezo film 602, and engages with an adhesive 603 to the lower frame 604. A wiring harness 605 and solder or welds 606 connect the wiring harness to the piezo film 602. The lower frame 604 has a concave surface, and the piezo film 602 engages with this curvature resulting in a piezo having a concave surface. The concave surface allows for increased reception of both high and low frequencies, thereby increasing sensitivity in certain instances, wherein peaks may be identified at these margins.

FIG. 17 particularly depicts the cross sectional view and side view of the film piezo 602, while FIG. 18 depicts the exploded view.

A curved film piezo can be exchanged for any of the piezos in embodiments described herein. For example, the lower frame 604 may comprise a relevant attachment means, and further comprise a PCB contact point to allow for direct exchange with prior examples and figures.

FIG. 19 depicts two different sensor pads 18 for use in an array with a piezo sensor. The sensor pads are angled at the skin facing surface, such that on the left hand side, the curvature on the bottom right engages to an angled structure to ensure a good acoustic fit. By contrast, the sensor pad on the right hand side of the page comprises a dual concave structure, to fit around a structure that is rounded. In each case, there is a proper fit, and so the sensor pod must be able to rotate to allow the sensor to be properly fit against the skin to achieve a proper acoustic contact for data collection. Cross-sectional views of the left and right sensor pads are depicted for clarity.

The sensor pods including both 85 and 86 components, are replaced, as necessary to allow for proper functioning of the piezo sensor. These replacements are performed as necessary, but at least every 10, 25, 50, 75, 100, 150, or 200 tests. When the sensor base 86 is replaced, the disposable piezo assembly 85 is also replaced. By contrast, in each test, sensor pads 18 are replaced.

In certain preferred embodiments, the sensor pads 18 can be secured onto the piezoelectric unit via an adhesive, such as one of several common low tack adhesives for providing for a temporary securing of the sensor pad to the piezo element. Other embodiments may utilize a gel or other water or solvent based material that may secure the sensor pads without the need for an additional adhesive material. In further embodiments, the sensor pad fits into the sensor pod and secures onto the piezo without the need for any adhesive.

A particular feature of the sensor pads described in the embodiments herein is the fact that the top face shape (that contacts the patient), and the bottom face shape (that contacts the piezo) are made so that when the top face contacts the patient and thus applies pressure to the sensor pad and through to the bottom face, the piezo does not flex when pressure is applied to the sensor pad. This is important to ensure consistency and accuracy of the piezo device. Therefore, the sensor pad, in certain embodiments, is designed such that the piezo does not flex when pressure is applied to the sensor pad. In a further preferred embodiment, the piezo flexes less than about 0.1%, 0.5%, 1.0%, 5.0%, 20%, and 25% and all percentages in between. Accordingly, in certain embodiments, the amount of flex is greater than zero (i.e. rigid and does not flex), but the amount of flex is minimized to maintain accuracy of the piezoelectric unit.

It is also preferred that the sensor pads create a proper impedance matching with a patient. Accordingly, the sensor pad is designed to have a slight tackiness which ensures a proper impedance matching with the patient, which then successfully transfers sounds through to the piezo element so that the piezo can properly detect vibrations and noise signals from the patient.

Therefore, in order to maintain both sterility of the medical device and proper function of the medical device, it is necessary to provide replaceable components. The entire device is a complex system comprising a display, a base unit, an array, a sensor base, a disposable piezo assembly, and a sensor pad. Each of the last four are disposable. The array itself can be disposed of after a number of uses, likely between 100-1000 uses. The array may lose elasticity to ensure proper fit on a patient, gain cracks, or simply lose stability. Each of these may increase variability and thus replacement is warranted.

The sensor base, comprises attachment means for the sensor pod to the array, and comprises electronics for connecting the sensor itself, typically a piezo, to the device. The base, using certain elastomeric materials to allow for movement of the sensor pod, will wear with time, necessitating replacement for minimizing variability.

The disposable piezo assembly is intended for more frequent replacement than the base or the array, as the piezo is susceptible to wear or damage. Accordingly, frequent changes, such as between every use and every 10, 25, 50, or 100 uses is necessary for accurate results.

The device is a complex system comprising multiple components, each working together to ensure that accurate results are obtained. Disposable components ensure that the system works properly, every time, and that it generates accurate and reliable data.

A kit is envisioned with the system, wherein a plurality of sensor pads are provided, a plurality of disposable piezo assemblies are provided, at least two sensor base assemblies, and at least two arrays. Said kit can be used with a system comprising the base and a display, as well as necessary software and hardware for energizing and running the device through its necessary protocols.

What is claimed is:

1. A sensor base for connecting to an array, said sensor base comprising:
   a diaphragm bellows membrane, a printed circuit board housing, a printed circuit board, and a locking cap;
   said diaphragm bellows membrane being a ring shape having an outer flange on an outer circumference of said ring, and an inner flange on an inner circumference of said ring;
   said outer flange engaging to said array and said inner flange engaging between said locking cap and said printed circuit board housing;
   said printed circuit board housing comprising a bell shape, having a narrow bottom and a wide top, with an opening between the top and bottom, a locking groove on said narrow bottom to engage said inner flange; and
   an attachment means at the wide top for securing a piezo assembly comprising a sensor; and
   said printed circuit board fitting within said opening.

2. The sensor base of claim 1 further comprising an adhesive to secure said printed circuit board to said printed circuit board housing.

3. The sensor base of claim 1, wherein said attachment means at the wide top is engaged with an outer edge of said wide top.

4. The sensor base of claim 3 wherein said attachment means are selected from the group consisting of: a magnet, one-half of a quarter turn locking mechanism, a groove, a pin, and threading.

5. The sensor base of claim 1, wherein said diaphragm bellows membrane is made of an elastomeric material.

6. A disposable sensor pod for connecting to an array, said disposable sensor pod comprising:
   a disposable piezo assembly; and
   a sensor base,
   wherein said disposable piezo assembly comprises:
   a circular piezo cap comprising a top, a bottom, an inner face, an outer face, and an opening between the piezo cap top and the piezo cap bottom, wherein the opening is larger at the top of the piezo cap than the bottom of the piezo cap;
   a flange comprising a top and a bottom, wherein said flange is positioned in the opening on the inner face at the top of the circular piezo cap;
   a piezo having a piezo top, a piezo bottom, and a piezo perimeter support, wherein said piezo is disposed within said piezo cap opening, wherein said piezo is engaged and adhered to the top of said flange via the piezo perimeter support;
   a printed circuit board contact board having a ring shape and an outer diameter to fit within the piezo cap opening, wherein the printed circuit board contact board is engaged to the bottom of said flange; and
   one-half of an attachment means on the inner face at the bottom of the circular piezo cap for securing said disposable piezo assembly to the sensor base,
   wherein the sensor base comprises:
   a diaphragm bellows membrane;
   a printed circuit board housing;
   a printed circuit board; and
   a locking cap,
   wherein said diaphragm bellows membrane has a ring shape comprising an outer flange on an outer circumference of said ring, and an inner flange on an inner circumference of said ring,
   wherein said outer flange is configured to engage said array and said inner flange is engaged between said locking cap and said printed circuit board housing,
   wherein said printed circuit board housing comprises a bell shape having a narrow bottom and a wide top, an opening between the wide top and narrow bottom, and a locking groove on said narrow bottom to engage said inner flange, wherein the printed circuit board is disposed within said printed circuit board housing opening; and a corresponding one-half of said attachment means at the wide top of the printed circuit board housing.

7. The disposable sensor pod of claim 6, wherein said attachment means are selected from the group consisting of: a magnet, one-half of a quarter turn locking mechanism, a groove, a pin, and threading.

8. The disposable sensor pod of claim 6, wherein the opening within the piezo cap is defined to receive a separately disposable skin contacting gel pad.

9. The disposable sensor pod of claim 6, wherein said diaphragm bellows membrane is made of an elastomeric material.

* * * * *